United States Patent
Bang et al.

(10) Patent No.: US 9,924,272 B2
(45) Date of Patent: Mar. 20, 2018

(54) METHOD AND APPARATUS FOR OUTPUTTING AUDIO IN ELECTRONIC DEVICE

(71) Applicant: Samsung Electronics Co., Ltd., Gyeonggi-do (KR)

(72) Inventors: Kyoung Ho Bang, Seoul (KR); Hyunchul Yang, Gyeonggi-do (KR); Juhwan Woo, Gyeonggi-do (KR); Jae Seong Lee, Gyeonggi-do (KR); Kyuhan Kim, Gyeonggi-do (KR); Namil Lee, Gyeonggi-do (KR); Juntai Kim, Gyeonggi-do (KR); Chulhwan Lee, Seoul (KR); Ho-Chul Hwang, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 0 days.

(21) Appl. No.: 15/171,598

(22) Filed: Jun. 2, 2016

(65) Prior Publication Data
US 2017/0048619 A1    Feb. 16, 2017

(30) Foreign Application Priority Data

Aug. 12, 2015 (KR) .......... 10-2015-0113979

(51) Int. Cl.
*H04R 5/04* (2006.01)
*H04R 3/04* (2006.01)
(Continued)

(52) U.S. Cl.
CPC .......... *H04R 5/04* (2013.01); *A61B 5/12* (2013.01); *G06F 3/162* (2013.01); *G06F 3/165* (2013.01);
(Continued)

(58) Field of Classification Search
CPC G06F 3/162; G06F 3/165; H04R 5/04; H04R 2420/07; H04W 8/005; H04W 8/18
(Continued)

(56) References Cited

U.S. PATENT DOCUMENTS 7,181,297 B1 * 2/2007 Pluvinage ............ A61B 5/0002
 381/60
7,283,635 B1 * 10/2007 Anderson ............... H04M 1/60
 381/384
(Continued)

FOREIGN PATENT DOCUMENTS

| KR | 1020060075134 | 7/2006 |
| KR | 1020130121632 | 11/2013 |
| WO | WO 2011/139502 | 11/2011 |

OTHER PUBLICATIONS

International Search Report dated Oct. 12, 2016 issued in counterpart application No. PCT/KR2016/006895, 11 pages.
(Continued)

*Primary Examiner* — Hemant Patel
(74) *Attorney, Agent, or Firm* — The Farrell Law Firm, P.C.

(57) ABSTRACT

A method and device for processing an audio output in consideration of the hearing characteristics of a user and the characteristics of an audio device connected to an electronic device is provided. The electronic device includes a user interface; an audio interface configured to establish a connection to an audio device, a memory, and at least one processor electrically connected to the user interface, the memory, and the audio interface, wherein the at least one processor is configured to acquire at least one of identification information of the audio device and characteristics of the audio device, select audio adaptation information,
(Continued)

change an audio signal, at least partially based on the audio adaptation information, and transmit the changed audio signal to the audio device.

15 Claims, 20 Drawing Sheets

(51) Int. Cl.
    *G06F 3/16*         (2006.01)
    *H04W 8/00*       (2009.01)
    *H04W 8/18*       (2009.01)
    *A61B 5/12*        (2006.01)
    *A61B 5/00*        (2006.01)

(52) U.S. Cl.
    CPC .............. *H04R 3/04* (2013.01); *H04W 8/005* (2013.01); *H04W 8/18* (2013.01); *A61B 5/7405* (2013.01); *H04R 2420/05* (2013.01); *H04R 2420/07* (2013.01); *H04R 2499/11* (2013.01)

(58) Field of Classification Search
    USPC ........................................................ 381/101
    See application file for complete search history.

(56) References Cited

U.S. PATENT DOCUMENTS

| | | | | |
|---|---|---|---|---|
| 8,059,833 B2 * | 11/2011 | Koh | ........................ | H04R 25/70 381/103 |
| 8,753,287 B2 | 6/2014 | Bang et al. | | |
| 2006/0140418 A1 | 6/2006 | Koh et al. | | |
| 2007/0078545 A1 * | 4/2007 | Hsieh | ........................ | H04S 7/30 700/94 |
| 2010/0027807 A1 | 2/2010 | Jeon | | |
| 2010/0119093 A1 | 5/2010 | Uzuanis et al. | | |
| 2011/0200217 A1 * | 8/2011 | Gurin | ..................... | A61B 5/123 381/320 |
| 2013/0178963 A1 | 7/2013 | Bergmann | | |
| 2013/0178964 A1 | 7/2013 | Bergmann | | |
| 2013/0236023 A1 * | 9/2013 | Horbach | .................. | H04R 5/04 381/59 |
| 2013/0287215 A1 | 10/2013 | Kim et al. | | |
| 2014/0079241 A1 * | 3/2014 | Chan | ....................... | H04H 20/86 381/77 |
| 2014/0086434 A1 | 3/2014 | Bang et al. | | |
| 2014/0153727 A1 | 6/2014 | Walsh et al. | | |
| 2014/0254828 A1 * | 9/2014 | Ray | ........................ | H03G 5/165 381/103 |
| 2014/0314261 A1 | 10/2014 | Selig et al. | | |
| 2014/0334644 A1 * | 11/2014 | Selig | ....................... | G06F 3/165 381/108 |
| 2015/0382096 A1 * | 12/2015 | Lamar | .................. | H04R 1/1041 381/74 |

OTHER PUBLICATIONS

European Search Report dated Dec. 19, 2016 issued in counterpart application No. 16174109.5-1910, 10 pages.
European Search Report dated Jul. 19, 2017 issued in counterpart application No. 16174109.5-1914, 7 pages.
Summons to Attend Oral Proceedings dated Nov. 15, 2017 issued in counterpart application No. 16174109.5-1914, 8 pages.

* cited by examiner

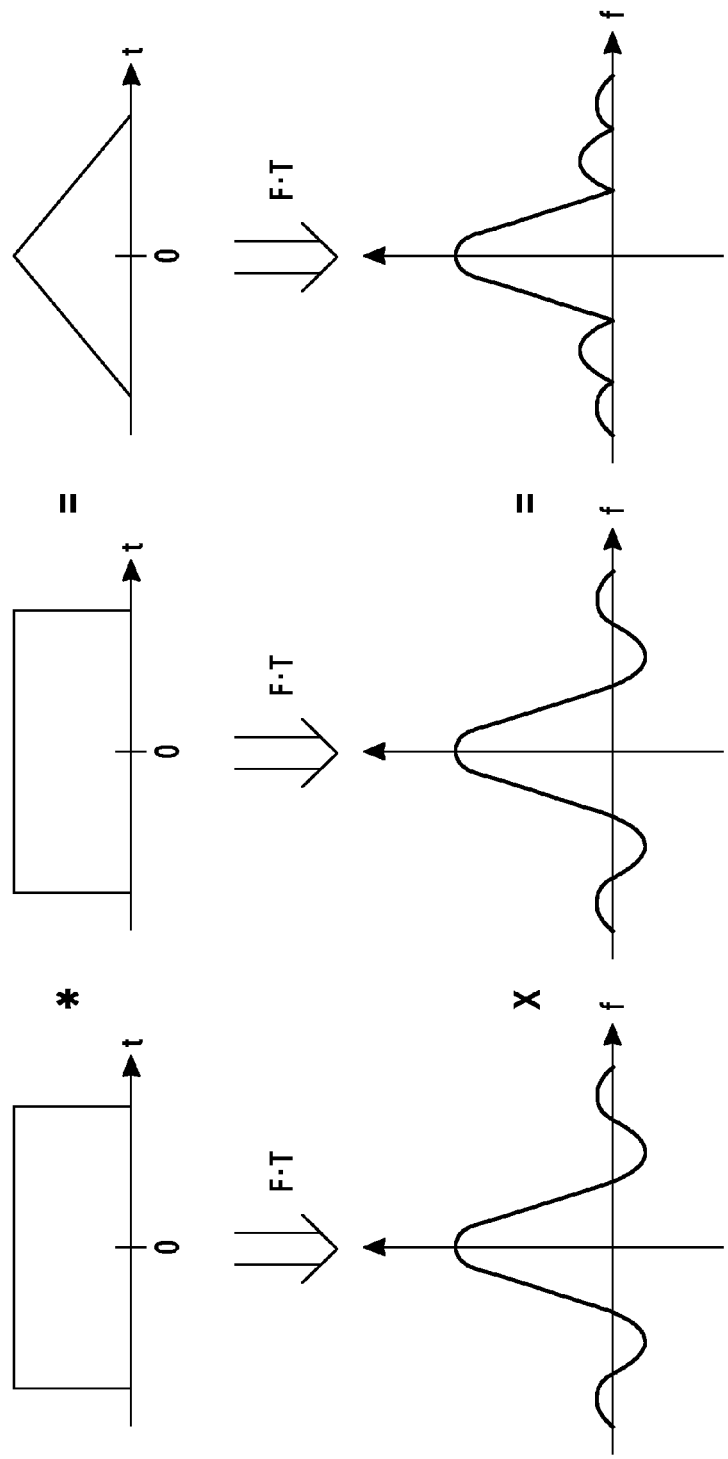

METHOD AND APPARATUS FOR OUTPUTTING AUDIO IN ELECTRONIC DEVICE

PRIORITY

This application claims priority under 35 U.S.C. § 119(a) to Korean Patent Application Serial No. 10-2015-0113979, which was filed in the Korean Intellectual Property Office on Aug. 12, 2015, the entire content of which is incorporated herein by reference.

BACKGROUND

1. Field of the Disclosure

The present disclosure generally relates to a method and device for outputting audio in an electronic device, and more particularly, to a method and device for processing an audio output in consideration of the hearing characteristics of a user and the characteristics of an audio device connected to an electronic device.

2. Description of the Related Art

With the recent development of digital technologies, various types of electronic devices such as a mobile communication terminal, a smart phone, a tablet personal computer (PC), a personal digital assistant (PDA), an electronic notebook, a notebook PC, a wearable device, and a television (TV) are widely used. Further, an electronic device may be connected to various types of audio devices (e.g. audio output devices, such as a wired headphone, a wired earphone, a wireless headphone, and a wireless earphone). The electronic device may output audio data (e.g., a sound source), which is being reproduced, through an audio device connected thereto and a user may listen to audio data of the electronic device through the audio device. The electronic device and the audio device may be connected to each other through a wired interface (e.g. a physical connector connection) or a wireless interface (e.g. Bluetooth connection).

Audio devices, which are used while connected to an electronic device, have different sound qualities and characteristics (e.g. frequency characteristic) according to the type of audio device (e.g. a wireless headphone, a wired headphone, a wireless earphone, and a wired earphone). For example, a low frequency band may be strengthened or a high frequency band may be equalized according to the characteristics of the audio device. Each audio device may have different frequency response characteristics. Therefore, an audio output from the electronic device may be provided to a user with different results according to the characteristics of the audio device. Moreover, when the characteristics of the audio device do not correspond to the hearing characteristics of the user, the user may be provided with different audio reproduction results.

SUMMARY

An aspect of the present disclosure provides a method and apparatus for outputting audio which may automatically convert an audio output in consideration of the characteristics of the audio device and the hearing characteristics of the user in an electronic device.

Another aspect of the present disclosure provides a method and apparatus for outputting audio, which may automatically update, when an audio device is changed, audio compensation information for compensating for the changed audio device and the hearing characteristics of a user in an electronic device.

Another aspect of the present disclosure provides a computer-readable recording medium having a program recorded therein to perform the method by a processor.

According to an aspect of the present disclosure, an electronic device is provided including a user interface, an audio interface configured to establish a connection to an audio device, a memory, and at least one processor electrically connected to the user interface, the memory, and the audio interface, wherein the at least one processor is configured to acquire at least one of identification information of the audio device and characteristics of the audio device, select audio adaptation information, change an audio signal, at least partially based on the audio adaptation information, and transmit the changed audio signal to the audio device.

According to another aspect of the present disclosure, an electronic device is provided including a communication interface configured to establish a connection to an audio device, a memory, and one or more processors that are electrically connected to the communication interface and the memory, wherein the one or more processors perform determining audio adaptation information related to the audio device in response to the connection of the audio device, correcting an audio output corresponding to the audio device on the basis of the audio adaptation information when the audio adaption information has been registered, and updating, when the audio adaption information has not been registered, the audio adaptation information related to the audio device and correcting an audio output corresponding to the characteristics of the audio device on the basis of the updated audio adaptation information.

According to another aspect of the present disclosure, an electronic device is provided including a wired or wireless interface configured to establish a connection to an audio device, a memory, and one or more processors that are electrically connected to the memory and the wired or wireless interface, wherein the memory, at the time of execution, may be configured to store instructions that instruct the one or more processors to, establish audio adaptation information on the basis of the frequency characteristics of the audio device and the hearing characteristics of a user, detect a connection of the audio device, determine audio adaptation information related to a connected audio device, convert a currently established audio output characteristic to an audio output characteristic corresponding to the connected audio device on the basis of the determined audio adaptation information, and process an audio output on the basis of the converted audio output characteristic.

According to another aspects of the present disclosure, an operation method of an electronic device is provided including detecting a connection of an audio device, acquiring at least one of identification information of the audio device and characteristics of the audio device, selecting audio adaptation information, changing an audio signal, at least partially based on the audio adaptation information, and transmitting the changed audio signal to the audio device.

According to another aspect of the present disclosure, an operation method of an electronic device is provided including detecting a connection of an audio device, determining audio adaptation information related to the audio device in response to the connection of the audio device, correcting an audio output corresponding to the audio device on the basis of the audio adaptation information when the audio adaption information has been registered, updating audio adaptation information related to the audio device when the audio adaption information has not been registered, and correcting an audio output corresponding to a characteristic of the audio device on the basis of the updated audio adaptation information.

According to another aspect of the present disclosure, a non-transitory recording medium includes a computer-readable non-transitory recording medium which records a program for executing in an electronic device, detecting a connection of an audio device, acquiring at least one of identification information and characteristics of the audio device, at least partially based on the connection to the audio device, selecting pre-stored audio adaptation information, at least partially based on the acquired information and/or characteristics, changing an audio signal, at least partially based on the audio adaptation information, and transmitting the changed audio signal to the audio device.

BRIEF DESCRIPTION OF THE DRAWINGS

The above and other aspects, features, and advantages of the present disclosure will be more apparent from the following detailed description taken in conjunction with the accompanying drawings, in which:

FIG. 20 illustrates a convolution method for creating a profile in an electronic device according to another embodiment of the present disclosure.

DETAILED DESCRIPTION

Figure 1:
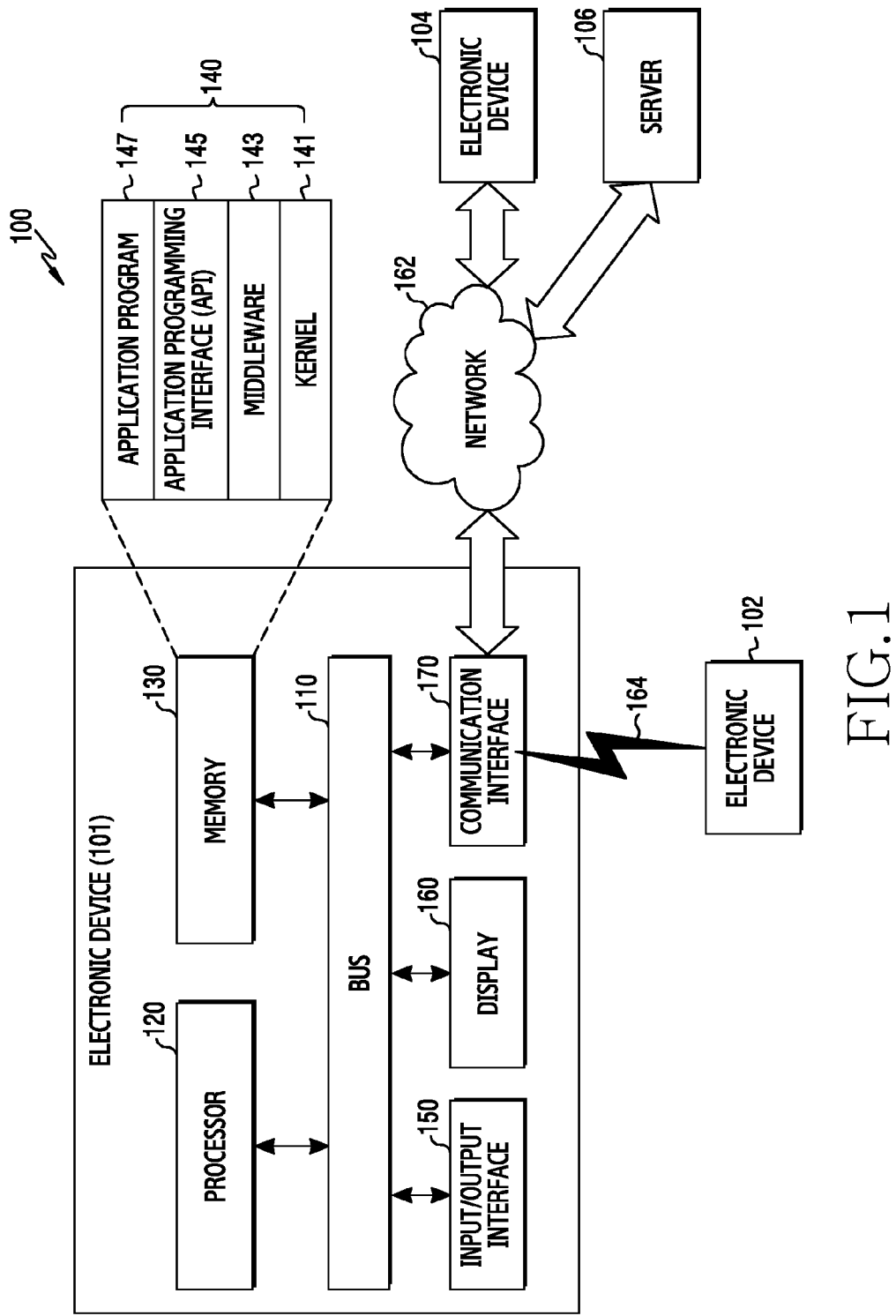
FIG. 1 illustrates a network environment including an electronic device, according to various embodiments of the present disclosure.

Hereinafter, various embodiments of the present disclosure will be described with reference to the accompanying drawings. However, it should be understood that the present disclosure is not limited to the particular forms disclosed herein, rather, the present disclosure should be construed to cover various modifications, equivalents, and/or alternatives of embodiments of the present disclosure. In describing the drawings, similar reference numerals may be used to designate similar constituent elements.

As used herein, the expressions "have", "may have", "include", or "may include" refers to the existence of a corresponding feature (e.g., numeral, function, operation, or constituent element such as component), and do not exclude one or more additional features.

In the present disclosure, the expressions "A or B", "at least one of A or/and B", or "one or more of A or/and B" may include all possible combinations of the items listed. For example, the expressions "A or B", "at least one of A and B", or "at least one of A or B" refer to all of (1) including at least one A, (2) including at least one B, or (3) including all of at least one A and at least one B.

The expressions "a first", "a second", "the first", or "the second" used in various embodiments of the present disclosure may modify various components regardless of the order and/or the importance but do not limit the corresponding components. For example, a first user device and a second user device indicate different user devices, although both of them are user devices. For example, a first element may be referred to as a second element, and similarly, a second element may be referred to as a first element without departing from the scope of the present disclosure.

It should be understood that when an element (e.g., first element) is referred to as being (operatively or communicatively) "connected," or "coupled," to another element (e.g., second element), it may be directly connected or coupled to the other element or any other element (e.g., third element) may be interposed between them. In contrast, it may be understood that when an element (e.g., first element) is referred to as being "directly connected," or "directly coupled" to another element (second element), there are no elements (e.g., third element) interposed between them.

The expression "configured to" used in the present disclosure may be used interchangeably with, for example, "suitable for", "having the capacity to", "designed to", "adapted to", "made to", or "capable of" according to the situation. The term "configured to" may not necessarily imply "specifically designed to" in hardware. Alternatively, in some situations, the expression "device configured to" may mean that the device, together with other devices or components, "is able to". For example, the phrase "processor adapted (or configured) to perform A, B, and C" may refer to a dedicated processor (e.g. embedded processor) only for performing the corresponding operations or a general-purpose processor (e.g., central processing unit (CPU) or application processor (AP)) that may perform the corresponding operations by executing one or more software programs stored in a memory device.

The terms used in the present disclosure are only used to describe specific embodiments, and do not limit the present disclosure. As used herein, singular forms may include plural forms as well, unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the same meanings as the contextual meanings in the relevant field of art, and are not to be interpreted to have ideal or excessively formal meanings unless clearly defined in the present disclosure. In some cases, even the terms defined in the present disclosure should not be interpreted to exclude embodiments of the present disclosure.

An electronic device according to various embodiments of the present disclosure may include a smart phone, a tablet personal computer (PC), a mobile phone, a video phone, an electronic book reader (e-book reader), a desktop PC, a laptop PC, a netbook computer, a workstation, a server, a personal digital assistant (PDA), a portable multimedia player (PMP), a MPEG-1 audio layer-3 (MP3) player, a mobile medical device, a camera, and a wearable device. The wearable device may include at least one of an accessory type (e.g., a watch, a ring, a bracelet, an anklet, a necklace, eyeglasses, contact lens, a head-mounted device (HMD)), fabric or clothing integrated type (e.g., an electronic clothing), a body-mounted type (e.g., a skin pad, or tattoo), and a bio-implantable type (e.g., an implantable circuit).

According to various embodiments of the present disclosure, the electronic device may be a home appliance. The home appliance may include a television, a digital video disk (DVD) player, an audio player, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ and PlayStation™), an electronic dictionary, an electronic key, a camcorder, and an electronic photo frame.

According to another embodiment of the present disclosure, the electronic device may include various medical devices (e.g., various portable medical measuring devices (a blood glucose monitoring device, a heart rate monitoring device, a blood pressure measuring device, a body temperature measuring device, etc.), a magnetic resonance angiography (MRA), a magnetic resonance imaging (MRI), a computed tomography (CT) machine, and an ultrasonic machine), a navigation device, a global positioning system (GPS) receiver, an event data recorder (EDR), a flight data recorder (FDR), a vehicle infotainment device, an electronic device for a ship (e.g., a navigation device for a ship, and a gyro-compass), avionics, security devices, an automotive head unit, a robot for home or industry, an automatic teller machine (ATM), point of sales (POS) terminal, or Internet of things (IoT) device (e.g., a light bulb, various sensors, electric or gas meter, a sprinkler device, a fire alarm, a thermostat, a streetlamp, a toaster, sporting goods, a hot water tank, a heater, a boiler, etc.).

According to various embodiments of the present disclosure, the electronic device may include at least one of a part of furniture or a building/structure, an electronic board, an electronic signature receiving device, a projector, and various types of measuring instruments (e.g., a water meter, an electric meter, a gas meter, and a radio wave meter). The electronic device may be a combination of one or more of the aforementioned various devices. The electronic device may be a flexible device. Further, the electronic device is not limited to the aforementioned devices, and may include a new electronic device according to the development of new technology.

Hereinafter, an electronic device according to various embodiments of the present disclosure will be described with reference to the accompanying drawings. As used herein, the term "user" may indicate a person who uses an electronic device or a device (e.g., an artificial intelligence electronic device) that uses an electronic device.

FIG. 1 illustrates a network environment including an electronic device according to various embodiments of the present disclosure.

An electronic device 101 within a network environment 100, according to various embodiments of the present disclosure, will be described with reference to FIG. 1. The electronic device 101 includes a bus 110, a processor 120, a memory 130, an input/output interface 150, a display 160, and a communication interface 170. The electronic device 101 may omit at least one of the above components or may further include other components.

The bus 110 may include, for example, a circuit which interconnects the components 110 to 170 and delivers a communication (e.g., a control message and/or data) between the components 110 to 170.

The processor 120 may include one or more of a central processing unit (CPU), an application processor (AP), and a communication processor (CP). The processor 120 may carry out, for example, calculation or data processing relating to control and/or communication of at least one other component of the electronic device 101.

The memory 130 may include a volatile memory and/or a non-volatile memory. The memory 130 may store, for example, commands or data relevant to at least one other component of the electronic device 101. According to an embodiment of the present disclosure, the memory 130 may store software and/or a program 140. The program 140 includes, for example, a kernel 141, middleware 143, an application programming interface (API) 145, and/or application programs (or "applications") 147. At least some of the kernel 141, the middleware 143, and the API 145 may be referred to as an operating system (OS).

The kernel 141 may control or manage system resources (e.g., the bus 110, the processor 120, or the memory 130) used for performing an operation or function implemented in the other programs (e.g., the middleware 143, the API 145, or the application programs 147). Furthermore, the kernel 141 may provide an interface through which the middleware 143, the API 145, or the application programs 147 may access the individual components of the electronic device 101 to control or manage the system resources.

The middleware 143, for example, may serve as an intermediary for allowing the API 145 or the application programs 147 to communicate with the kernel 141 to exchange data.

The middleware 143 may process one or more task requests received from the application programs 147 according to assigned priorities. For example, the middleware 143 may assign priorities for using the system resources (e.g., the bus 110, the processor 120, the memory 130, and the like) of the electronic device 101, to at least one of the application programs 147. For example, the middleware 143 may perform scheduling or load balancing on the one or more task requests by processing the one or more task requests according to the assigned priorities.

The API 145 is an interface through which the applications 147 control functions provided from the kernel 141 or the middleware 143, and may include, for example, at least one interface or function (e.g., instruction) for file control, window control, image processing, character control, and the like.

The input/output interface 150 may function as an interface that transfers commands or data input from a user or another external device to the other element(s) of the electronic device 101. Furthermore, the input/output interface 150 may output the commands or data received from the other element(s) of the electronic device 101 to the user or another external device.

The display 160 may include a liquid crystal display (LCD), a light-emitting diode (LED) display, an organic light-emitting diode (OLED) display, a microelectromechanical systems (MEMS) display, and an electronic paper display. The display 160 may display, for example, various types of content (e.g., text, images, videos, icons, or symbols) to users. The display 160 may include a touch screen, and may receive, for example, a touch, gesture, proximity, or hovering input using an electronic pen or a user's body part.

The communication interface 170 may establish communication, for example, between the electronic device 101 and a first external electronic device 102, a second external electronic device 104, or a server 106. For example, the communication interface 170 may be connected to a network 162 through wireless or wired communication, and may communicate with the second external electronic device 104 or the server 106. The wireless communication may use at least one of, for example, long term evolution (LTE), LTE-advanced (LTE-A), code division multiple access (CDMA), wideband CDMA (WCDMA), universal mobile telecommunications system (UMTS), wireless broadband (WiBro), and global system for mobile communications (GSM), as a cellular communication protocol. In addition, the wireless communication may include, for example, short range communication 164. The short-range communication 164 may include at least one of, for example, Wi-Fi, Bluetooth, near field communication (NFC), and global navigation satellite system (GNSS). GNSS may include, for example, at least one of global positioning system (GPS), global navigation satellite system (Glonass), Beidou navigation satellite system (Beidou) or Galileo, and the European global satellite-based navigation system, based on a location, a bandwidth, and the like. Hereinafter, in the present disclosure, the "GPS" may be interchangeably used with the "GNSS". The wired communication may include, for example, at least one of a universal serial bus (USB), a high definition multimedia interface (HDMI), recommended standard 232 (RS-232), and a plain old telephone service (POTS). The network 162 may include at least one of a telecommunication network such as a computer network (e.g., a LAN or a WAN), the Internet, and a telephone network.

Each of the first and second external electronic devices 102 and 104, may be of a type identical to or different from that of the electronic device 101. According to an embodiment of the present disclosure, the server 106 may include a group of one or more servers.

According to various embodiments of the present disclosure, all or some of the operations performed in the electronic device 101 may be executed in another electronic device or a plurality of electronic devices (e.g., the electronic devices 102 and 104 or the server 106). When the electronic device 101 has to perform some functions or services automatically or in response to a request, the electronic device 101 may request another electronic device 102 or 104 or the server 106, to execute at least some functions relating thereto instead of, or in addition to, autonomously performing the functions or services. Another electronic device 102 or 104, or the server 106 may execute the requested functions or the additional functions, and may deliver a result of the execution to the electronic device 101. The electronic device 101 may process the received result as it is or additionally, and may provide the requested functions or services. To this end, for example, cloud computing, distributed computing, or client-server computing technologies may be used.

Figure 2:
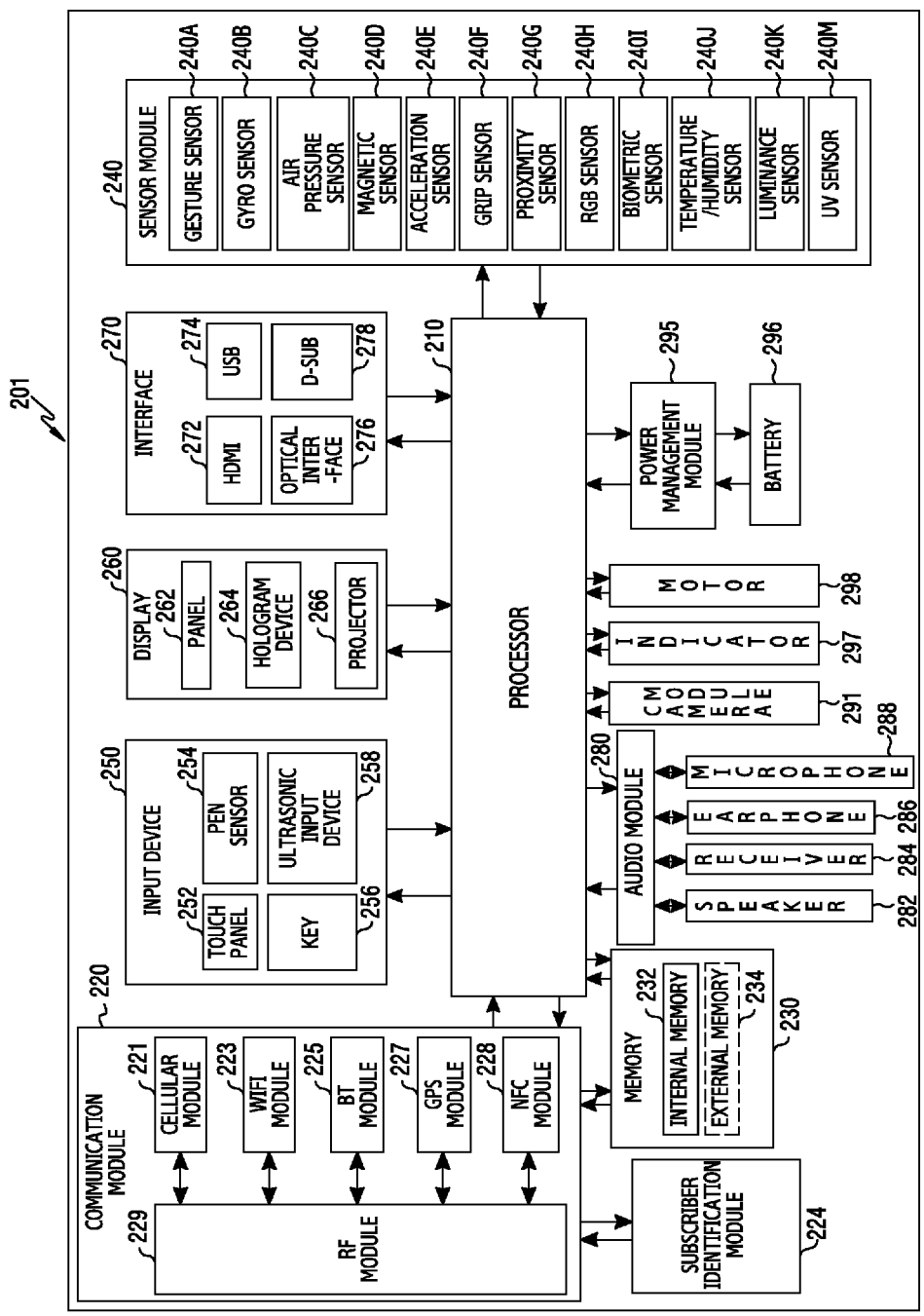
FIG. 2 is a block diagram illustrating an electronic device, according to various embodiments of the present disclosure.

FIG. 2 is a block diagram of an electronic device according to various embodiments of the present disclosure.

The electronic device 201 may include, for example, the entire or a part of the electronic device 101 shown in FIG. 1. The electronic device 201 includes one or more processors 210 (e.g., application processors (AP)), a communication module 220, a subscriber identification module (SIM) 224, a memory 230, a sensor module 240, an input device 250, a display 260, an interface 270, an audio module 280, a camera module 291, a power management module 295, a battery 296, an indicator 297, and a motor 298.

The processor 210 may control a plurality of hardware or software components connected to the processor 210 by driving an operating system or an application program, and perform processing of various types of data and calculations. The processor 210 may be embodied as, for example, a system on chip (SoC). According to an embodiment of the present disclosure, the processor 210 may further include a graphic processing unit (GPU) and/or an image signal processor. The processor 210 may include at least some (for example, a cellular module 221) of the components illustrated in FIG. 2. The processor 210 may load, into a volatile memory, commands or data received from at least one (e.g., a non-volatile memory) of the other components and may process the loaded commands or data, and may store various data in a non-volatile memory.

The communication module 220 may have a configuration equal or similar to that of the communication interface 170 of FIG. 1. The communication module 220 includes a cellular module 221, a Wi-Fi module 223, a BT module 225, a GNSS module 227 (e.g., a GPS module 227, a Glonass module, a Beidou module, or a Galileo module), an NFC module 228, and a radio frequency (RF) module 229.

The cellular module 221, for example, may provide a voice call, a video call, a text message service, or an Internet access service through a communication network. According to an embodiment of the present disclosure, the cellular module 221 may distinguish and authenticate the electronic device 201 in a communication network using the SIM card 224. The cellular module 221 may perform at least some of the functions that the AP 210 may provide. The cellular module 221 may include a communication processor (CP).

Each of the Wi-Fi module 223, the BT module 225, the GNSS module 227, and the NFC module 228 may include a processor for processing data transmitted/received through a corresponding module. According to an embodiment of the present disclosure, at least some (e.g., two or more) of the cellular module 221, the Wi-Fi module 223, the BT module 225, the GNSS module 227, and the NFC module 228 may be included in one integrated chip (IC) or IC package.

The RF module 229, for example, may transmit/receive a communication signal (e.g., an RF signal). The RF module 229 may include, for example, a transceiver, a power amplifier module (PAM), a frequency filter, a low noise amplifier (LNA), and an antenna. According to another embodiment of the present disclosure, at least one of the cellular module 221, the WIFI module 223, the BT module 225, the GNSS module 227, and the NFC module 228 may transmit/receive an RF signal through a separate RF module.

The SIM 224 may include a card including an embedded SIM, and may contain unique identification information (e.g., an integrated circuit card identifier (ICCID)) or subscriber information (e.g., an international mobile subscriber identity (IMSI)).

The memory 230 (e.g., the memory 130) includes an embedded memory 232 or an external memory 234. The embedded memory 232 may include at least one of a volatile memory (e.g., a dynamic random access memory (DRAM), a static RAM (SRAM), a synchronous dynamic RAM (SDRAM), and the like) and a non-volatile memory (e.g., a one time programmable read only memory (OTPROM), a programmable ROM (PROM), an erasable and programmable ROM (EPROM), an electrically erasable and programmable ROM (EEPROM), a mask ROM, a flash ROM, a flash memory (e.g., a NAND flash memory or a NOR flash memory), a hard disc drive, a solid state drive (SSD), and the like).

The external memory 234 may further include a flash drive, for example, a compact flash (CF), a secure digital (SD), a micro secure digital (Micro-SD), a mini secure digital (Mini-SD), an extreme digital (xD), a multimediacard (MMC), a memory stick, and the like. The external memory 234 may be functionally and/or physically connected to the electronic device 201 through various interfaces.

The sensor module 240, for example, may measure a physical quantity or detect an operation state of the electronic device 201, and may convert the measured or detected information into an electrical signal. The sensor module 240 includes at least one of a gesture sensor 240A, a gyro sensor 240B, an atmospheric pressure sensor (barometer) 240C, a magnetic sensor 240D, an acceleration sensor 240E, a grip sensor 240F, a proximity sensor 240G, a color sensor 240H (e.g., red, green, and blue (RGB) sensor), a biometric sensor (medical sensor) 240I, a temperature/humidity sensor 240J, an illuminance sensor 240K, and a ultra violet (UV) sensor 240M. Additionally or alternatively, the sensor module 240 may include, for example, an E-nose sensor, an electromyography (EMG) sensor, an electroencephalogram (EEG) sensor, an electrocardiogram (ECG) sensor, an infrared (IR) sensor, an iris scan sensor, and/or a fingerprint scan sensor. The sensor module 240 may further include a control circuit for controlling one or more sensors included therein. According to an embodiment of the present disclosure, the electronic device 201 may further include a processor configured to control the sensor module 240, as a part of the processor 210 or separately from the processor 210, and may control the sensor module 240 while the processor 210 is in a sleep state.

The input device 250 may include, for example, a touch panel 252, a (digital) pen sensor 254, a key 256, or an ultrasonic input device 258. The touch panel 252 may use, for example, at least one of a capacitive type, a resistive type, an infrared type, and an ultrasonic type. The touch panel 252 may further include a control circuit. The touch panel 252 may further include a tactile layer, and provide a tactile reaction to the user.

The (digital) pen sensor 254 may include, for example, a recognition sheet which is a part of the touch panel or is separated from the touch panel. The key 256 may include, for example, a physical button, an optical key or a keypad. The ultrasonic input device 258 may detect, through a microphone 288, ultrasonic waves generated by an input tool, and identify data corresponding to the detected ultrasonic waves.

The display 260 (e.g., the display 160) may include a panel 262, a hologram device 264, or a projector 266. The panel 262 may include a configuration identical or similar to the display 160 illustrated in FIG. 1. The panel 262 may be flexible, transparent, or wearable. The panel 262 may be embodied as a single module with the touch panel 252. The hologram device 264 may show a three dimensional (3D) image in the air by using an interference of light. The projector 266 may project light onto a screen to display an image. The screen may be located, for example, in the interior of, or on the exterior of, the electronic device 201. According to an embodiment of the present disclosure, the display 260 may further include a control circuit for controlling the panel 262, the hologram device 264, or the projector 266.

The interface 270 may include, for example, a high-definition multimedia interface (HDMI) 272, a universal serial bus (USB) 274, an optical interface 276, or a d-sub-miniature (D-sub) 278. The interface 270 may be included in, for example, the communication interface 170 illustrated in FIG. 1. Additionally or alternatively, the interface 270 may include, for example, a mobile high-definition link (MHL) interface, a secure digital (SD) card/multi-media card (MMC) interface, or an infrared data association (IrDA) standard interface.

The audio module 280, for example, may bidirectionally convert a sound and an electrical signal. At least some components of the audio module 280 may be included in, for example, the input/output interface 150 illustrated in FIG. 1. The audio module 280 may process voice information input or output through, for example, a speaker 282, a receiver 284, earphones 286, or the microphone 288.

The camera module 291 may photograph a still image and a video. According to an embodiment of the present disclosure, the camera module 291 may include one or more image sensors (e.g., a front sensor or a back sensor), a lens, an image signal processor (ISP) or a flash (e.g., LED or xenon lamp).

The power management module 295 may manage, for example, power of the electronic device 201. According to an embodiment of the present disclosure, the power management module 295 may include a power management integrated circuit (PMIC), a charger integrated circuit (IC), or a battery gauge. The PMIC may use a wired and/or wireless charging method. Examples of the wireless charging method may include, for example, a magnetic resonance method, a magnetic induction method, an electromagnetic wave method, and the like. Additional circuits (e.g., a coil loop, a resonance circuit, a rectifier, etc.) for wireless charging may be further included. The battery gauge may measure, for example, a residual charge quantity of the battery 296, and a voltage, a current, or a temperature while charging. The battery 296 may include, for example, a rechargeable battery and/or a solar battery.

The indicator 297 may display a particular state (e.g., a booting state, a message state, a charging state, and the like) of the electronic device 201 or a part (e.g., the processor 210) of the electronic device 201. The motor 298 may convert an electrical signal into a mechanical vibration, and may generate a vibration, a haptic effect, and the like. The electronic device 201 may include a processing device (e.g., a GPU) for supporting a mobile TV. The processing device for supporting a mobile TV may process, for example, media data according to a certain standard such as digital multimedia broadcasting (DMB), digital video broadcasting (DVB), or mediaFLO™.

Each of the above-described component elements of hardware according to the present disclosure, may be configured with one or more components, and the names of the corresponding component elements may vary based on the type of electronic device. In various embodiments, the electronic device may include at least one of the above-described elements. Some of the above-described elements may be omitted from the electronic device, or the electronic device may further include additional elements. Also, some of the components according to various embodiments may be combined into one entity, which may perform functions identical to those of the relevant components before the combination.

Figure 3:
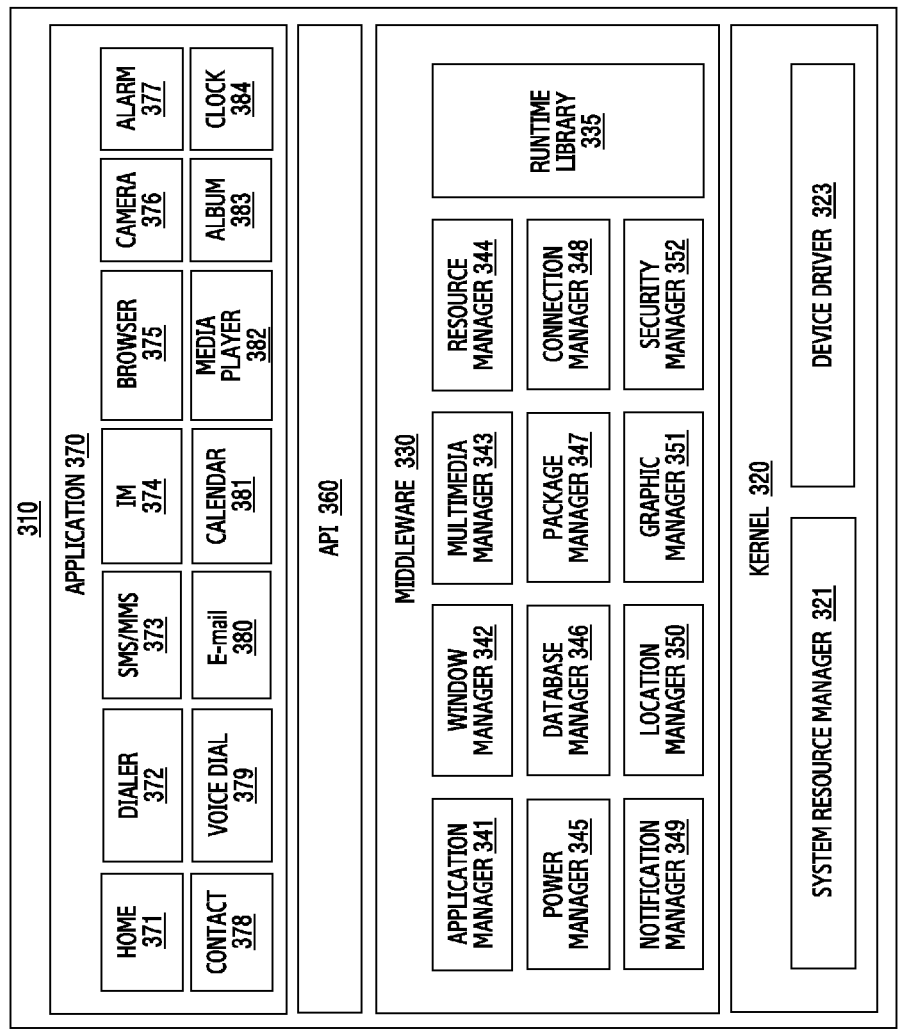
FIG. 3 is a block diagram illustrating a program module, according to various embodiments of the present disclosure.

FIG. 3 is a block diagram of a program module according to various embodiments of the present disclosure.

According to an embodiment of the present disclosure, the program module 310 (e.g., the program 140) may include an operating system (OS) for controlling resources related to the electronic device (e.g., the electronic device 101) and/or various applications (e.g., the application programs 147) executed in the operating system. The operating system may be, for example, Android, iOS, Windows, Symbian, Tizen, Bada, and the like.

The program module 310 includes a kernel 320, middleware 330, an API 360, and/or applications 370. At least some of the program module 310 may be preloaded on an electronic device, or may be downloaded from an external electronic device 102 or 104, or the server 106.

The kernel 320 (e.g., the kernel 141) includes a system resource manager 321 and/or a device driver 323. The system resource manager 321 may control, allocate, or collect system resources. According to an embodiment of the present disclosure, the system resource manager 321 may include a process management unit, a memory management unit, a file system management unit, and the like. The device driver 323 may include, for example, a display driver, a camera driver, a Bluetooth driver, a shared memory driver, a USB driver, a keypad driver, a Wi-Fi driver, an audio driver, or an inter-process communication (IPC) driver.

The middleware 330 may provide a function required in common by the applications 370, or may provide various functions to the applications 370 through the API 360 so as to enable the applications 370 to efficiently use the limited system resources in the electronic device. According to an embodiment of the present disclosure, the middleware 330 (e.g., the middleware 143) includes a run time library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 may include a library module that a compiler uses in order to add a new function through a programming language while an application 370 is being executed. The runtime library 335 may perform input/output management, memory management, an arithmetic function, and the like.

The application manager 341 may manage, for example, a life cycle of at least one of the applications 370. The window manager 342 may manage graphical user interface (GUI) resources used by a screen. The multimedia manager 343 may recognize a format required for reproduction of various media files, and may perform encoding or decoding of a media file by using a codec suitable for the corresponding format. The resource manager 344 may manage resources of a source code, a memory, and a storage space of at least one of the applications 370.

The power manager 345 may operate together with, for example, a basic input/output system (BIOS) and the like, to manage a battery or power source and may provide power information and the like, required for the operations of the electronic device. The database manager 346 may generate, search a memory for, and/or change a database to be used by at least one of the applications 370. The package manager 347 may manage installation or an update of an application distributed in a form of a package file.

The connectivity manager 348 may manage wireless connectivity such as Wi-Fi or Bluetooth. The notification manager 349 may display or notify of an event such as an arrival message, proximity notification, and the like, in such a way that does not disturb a user. The location manager 350 may manage location information of an electronic device. The graphic manager 351 may manage a graphic effect which will be provided to a user, or a user interface related to the graphic effect. The security manager 352 may provide all security functions required for system security, user authentication, and the like. According to an embodiment of the present disclosure, when the electronic device (e.g., the electronic device 101) has a telephone call function, the middleware 330 may further include a telephony manager for managing a voice call function or a video call function of the electronic device.

The middleware 330 may include a middleware module that forms a combination of various functions of the above-described components. The middleware 330 may provide a module specialized for each OS in order to provide a differentiated function. Further, the middleware 330 may dynamically remove some of the existing components or add new components.

The API 360 (e.g., the API 145) is, for example, a set of API programming functions, and may be provided with a different configuration according to an OS. For example, in the case of Android or iOS, one API set may be provided for each platform. In the case of Tizen, two or more API sets may be provided for each platform.

The applications 370 include one or more applications which may provide functions such as a home 371, a dialer 372, an SMS/MMS 373, an instant message (IM) 374, a browser 375, a camera 376, an alarm 377, contacts 378, a voice dial 379, an email 380, a calendar 381, a media player 382, an album 383, a clock 384, health care (e.g., measuring exercise quantity or blood sugar levels), or environment information (e.g., providing atmospheric pressure, humidity, or temperature information).

According to an embodiment of the present disclosure, the applications 370 may include an information exchange application that supports exchanging information between the electronic device 101 and an external electronic device 102 or 104. The information exchange application may include, for example, a notification relay application for transferring specific information to an external electronic device or a device management application for managing an external electronic device.

For example, the notification relay application may include a function of transferring, to the external electronic device 102 or 104, notification information generated from other applications of the electronic device 101 (e.g., an SMS/MMS application, an e-mail application, a health management application, or an environmental information application). Further, the notification relay application may receive notification information from, for example, an external electronic device 102 or 104, and provide the received notification information to a user.

The device management application may manage (e.g., install, delete, or update), for example, at least one function of an external electronic device 102 or 104, communicating with the electronic device (e.g., a function of turning on/off the external electronic device itself (or some components) or a function of adjusting the brightness (or a resolution) of the display), applications operating in the external electronic device, and services provided by the external electronic device (e.g., a call service or a message service).

According to an embodiment of the present disclosure, the applications 370 may include applications (e.g., a health care application of a mobile medical appliance and the like) designated according to an external electronic device 102 or 104. The applications 370 may include an application received from an external electronic device 102 or 104 or the server 106. The applications 370 may include a preloaded application or a third party application that may be downloaded from a server 106. The names of the components of the program module 310 according to an embodiment of the present disclosure may change according to the type of operating system.

At least a part of the programming module 310 may be implemented in software, firmware, hardware, or a combination of two or more thereof. At least some of the program module 310 may be implemented (e.g., executed) by, for example, the processor (e.g., the processor 1410). At least some of the program module 310 may include, for example, a module, a program, a routine, a set of instructions, and/or a process for performing one or more functions.

The term "module" as used herein may, for example, refer to a unit including one of hardware, software, or firmware or a combination of two or more of them. The term "module" may be interchangeably used with, for example, the terms "unit", "logic", "logical block", "component", or "circuit". The "module" may be a minimum unit of an integrated component element or a part thereof. The "module" may be a minimum unit for performing one or more functions or a part thereof. The "module" may be mechanically or electronically implemented. For example, the "module" according to an embodiment of the present disclosure may include at least one of an application-specific integrated circuit (ASIC) chip, a field-programmable gate arrays (FPGA), and a programmable-logic device for performing operations which has been known or are to be developed hereinafter.

At least some of the devices (for example, modules or functions thereof) or the method (for example, operations) according to an embodiment of the present disclosure may be implemented by a command stored in a non-transitory computer-readable storage medium in a programming module form. The instruction, when executed by a processor (e.g., the processor 120), may cause the one or more processors to execute the function corresponding to the instruction. The non-transitory computer-readable recoding medium may be, for example, the memory 130.

The non-transitory computer readable recoding medium may include a hard disk, a floppy disk, magnetic media (e.g., a magnetic tape), optical media (e.g., a compact disc read only memory (CD-ROM) and a digital versatile disc (DVD)), magneto-optical media (e.g., a floptical disk), a hardware device (e.g., a read only memory (ROM), a random access memory (RAM), a flash memory), and the like. In addition, the program instructions may include high level language codes, which may be executed in a computer by using an interpreter, as well as machine codes made by a compiler. The aforementioned hardware device may be configured to operate as one or more software modules in order to perform the operations of the present disclosure, and vice versa.

Any of the modules or programming modules according to various embodiments of the present disclosure may include at least one of the above described elements, exclude some of the elements, or further include other additional elements. The operations performed by the modules, programming module, or other elements according to various embodiments of the present disclosure may be executed in a sequential, parallel, repetitive, or heuristic manner. Further, some operations may be executed according to another order or may be omitted, or other operations may be added.

Various embodiments disclosed herein are provided merely to describe technical details of the present disclosure and to help the understanding of the present disclosure, and do not limit the scope of the present disclosure. Therefore, it should be construed that all modifications and changes or modified and changed forms based on the technical idea of the present disclosure fall within the scope of the present disclosure.

Various embodiments of the present disclosure disclose a method and apparatus for outputting audio. The method and apparatus may automatically convert an audio output and may output the converted audio output, according to the characteristics (e.g. frequency characteristics) of an audio device, which are combined with hearing characteristics, when a user connects the audio device to an electronic device and uses an audio solution considering the hearing characteristics of the user. Various embodiments of the present disclosure disclose a method and apparatus for outputting audio, which may automatically update and establish audio compensation information in consideration of the characteristics of a connected audio device and the hearing characteristics of a user when a connection of an audio device, in which audio compensation information (or audio adaptation information) (e.g. profile, frequency information) for compensating for an audio output characteristic according to each audio device in an electronic device is not established, is detected.

The electronic device, according to the various embodiments of the present disclosure, may include all information and communication devices, multimedia devices, wearable devices, and all application devices thereof that use one or more various processors, such as an application processor (AP), a communication processor (CP), a Graphic Processing Unit (GPU), a central processing unit (CPU), and the like.

Hereinafter, the method and apparatus for outputting audio will be described with reference to the accompanying drawings. However, since the various embodiments are not restricted or limited by the following description, it should be noted that software applications may be made that will be described below. Hereinafter, various embodiments of the present disclosure will be described based on a hardware approach. However, various embodiments of the present disclosure include a technology that uses both hardware and software and thus, the present disclosure may not exclude the use of software.

Figure 4:
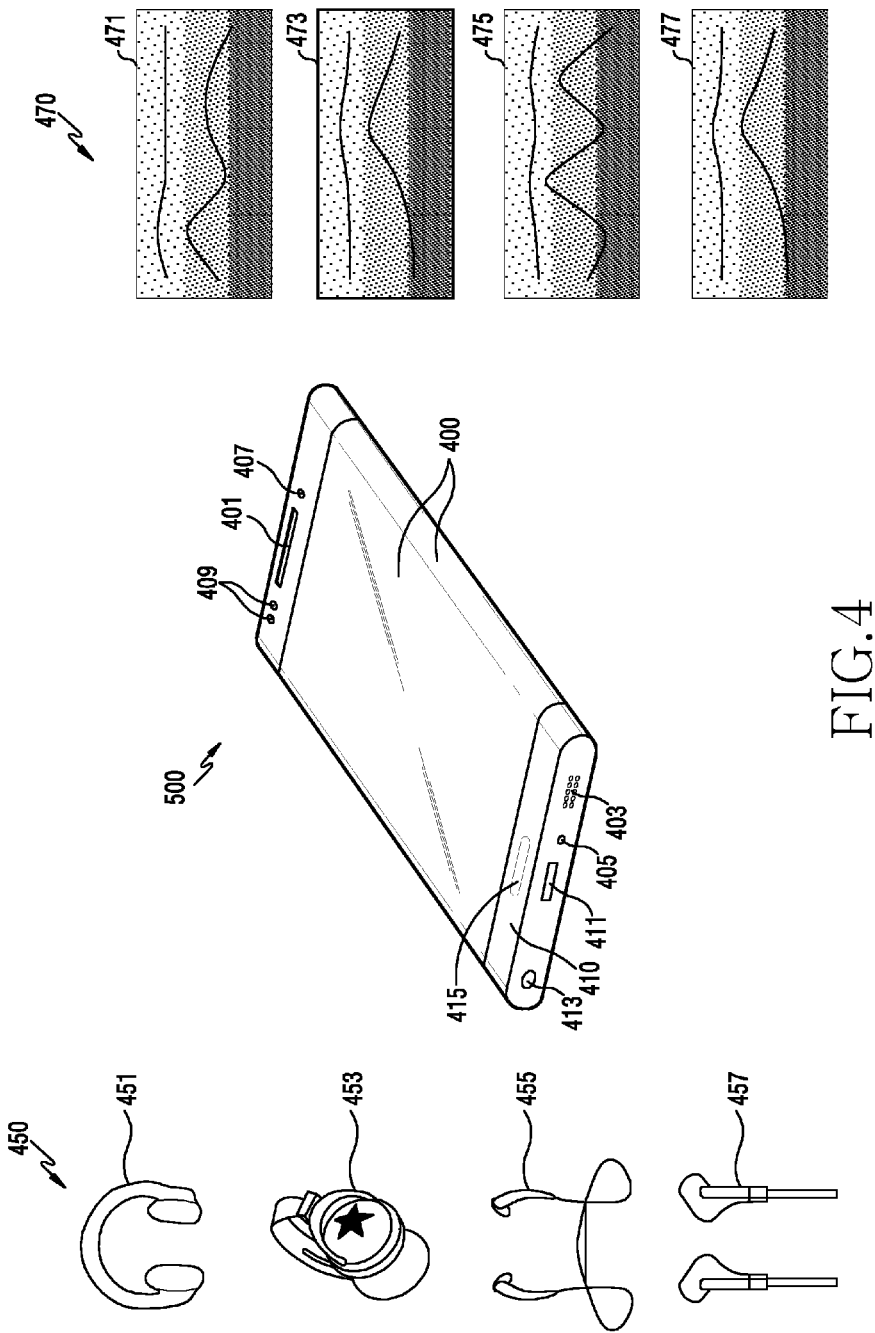
FIG. 4 illustrates processing an audio output according to a characteristic of a connected audio device in an electronic device, according to various embodiments of the present disclosure.

FIG. 4 illustrates processing an audio output according to a characteristic of a connected audio device in an electronic device according to various embodiments of the present disclosure. Referring to FIG. 4, a system may include an audio device 450 and an electronic device 500.

Referring to FIG. 4, the audio device 450 may include an audio output device which is wired or wirelessly connected to the electronic device 500, receives audio data reproduced in the electronic device 500, and outputs the received audio through a speaker in the audio output device. The audio device 450 includes various devices, such as a wired headphone 451, a wireless headphone 453 (e.g. Bluetooth headphone), a wireless earphone 455 (e.g. Bluetooth earphone), and a wired earphone 457, which may be wired or wirelessly connected to the electronic device 500.

Referring to FIG. 4, the electronic device 500 includes a display 400, a housing (or main body) on which the display 400 is mounted and fastened, and an additional device which is formed on the housing 410 and performs a function of the electronic device. The additional device includes a first speaker 401, a second speaker 403, a microphone 405, a front camera module 407, an illumination sensor 409, a charging or data input/output port 411, an audio input/output port 413, and a button 415.

According to various embodiments of the present disclosure, the display 400 may include a flexible display which may be bent, curved, or rolled without damage through a substrate as thin and flexible as paper. The curved display has a feature of being coupled to the housing 410 and remaining in a curved form. The electronic device 500 may also be implemented as a display device, which may be freely bent or unbent, such as a flexible display, including the curved display. The display 400 may replace a glass substrate covering a liquid crystal with a plastic film so as to provide flexibility by which the display may be folded or unfolded in a liquid crystal display (LCD), a light emitting diode (LED), an organic LED (OLED), and an active matrix OLED (AMOLED). The display 400 may extend up to at least one side (e.g. at least one of a left side, a right side, an upper side, and a lower side) of the electronic device 500, be folded in a radius of curvature (e.g. 5 cm, 1 cm, 7.5 mm, 5 mm, 4 mm, etc.) less than a radius of curvature in which the curved display may be operated, and be fastened at a side of the housing 410.

According to various embodiments of the present disclosure, when the audio device 450 is connected, the electronic device 500 may determine audio compensation information 470 (e.g. a profile, frequency information, and the like, which are audio adaptation information) corresponding to the audio device 450.

According to an embodiment of the present disclosure, the electronic device 500 may detect that the audio device 450 is connected, and may search a memory for and select, in response to the detection of the connection of the audio device 450, a particular profile related to the connected audio device 450 (e.g. audio adaptation information for the audio device 450) from among profiles pre-established according to identification information and/or characteristics of the audio device 450 (e.g. device identifier (e.g. ID)). The electronic device 500 may automatically change a currently established profile to the selected profile for an audio output and compensate for the audio output according to the changed profile. The profile may be, for example, information which is registered in advance by combining the hearing characteristics of a user with a basic frequency characteristic of the audio device by using such a method as convolution. A profile is used to provide audio having sound quality optimized for a user by considering the characteristics of an audio device and the hearing characteristics of the user, and may indicate information established in order to compensate for an audio output characteristic according to each audio device.

According to an embodiment of the present disclosure, the electronic device 500 may detect a connection of the audio device 450 thereto, and may search a memory for and select, in response to the detection of the connection of the audio device 450, particular frequency information related specifically to the audio device 450 from among frequency information pre-established according to a frequency characteristic of the audio device 450. The electronic device 500 may automatically change currently established frequency information to the selected frequency information for an audio output, and may combine the changed frequency information and the hearing characteristics of a user so as to compensate for the audio output. For example, the electronic device 500 may combine the frequency information of an audio device and the hearing characteristics of a user so as to create a profile related to a currently connected audio device, and may compensate for an audio output on the basis of the created profile.

According to various embodiments of the present disclosure, multiple pieces of information may be stored in the audio compensation information 470 according to each audio device 450. A first audio compensation information 471 may be established for the wired headphone 451, a second audio compensation information 473 may be established for the wireless headphone 453, a third audio compensation information 475 may be established for the wireless earphone 455, and a fourth audio compensation information 477 may be established for the wired earphone 457. The audio compensation information 470, such as the first audio compensation information 471, the second audio compensation information 473, the third audio compensation information 475, and the fourth audio compensation information 477, may be established in advance in consideration of the hearing characteristics of a user and the characteristics of the audio device 450. The audio compensation information 477 may be created in real time in consideration of the characteristics of the connected audio device 450 and the hearing characteristics of the user and then stored in the electronic device 500.

According to an embodiment of the present disclosure, when the connection of the wireless headphone 453 is detected through Bluetooth communication, the electronic device 500 may determine the audio compensation information 473 (e.g. a profile or frequency information) corresponding to the wireless headphone 453 from among multiple pieces of pre-established audio compensation information 470, and may process an operation related to audio compensation and output audio in response to the determined audio compensation information 473. For example, the electronic device 500 may process an audio output in consideration of an equal loudness curve and thus may improve a sound quality which a user hears. The equal loudness curve may show levels of sounds generated in pure sine waves of different frequencies when a person without hearing impairment listens to the sounds and perceives the sounds as equally loud. Generally, even a sound having physically equal loudness may sound different to a person's ears according to the frequency. For example, in order for the person's ears to hear a 60-phon sound, a 1 KHz sine wave should be at a sound pressure level (SPL) of 60 dB and a 100 Hz sine wave should be at an SPL of 78 dB. As described above, even a sound having equal loudness may be heard different according to a frequency. In consideration of this point, sound pressure levels according to respective frequencies, which sound like sounds having equal loudness, are experimentally determined, the determined sound pressure levels are on an equal loudness curve.

According to various embodiments of the present disclosure, examples of compensating and outputting audio according to the characteristics of the audio device 450 will be described with reference to the accompanying drawings.

Figure 5:
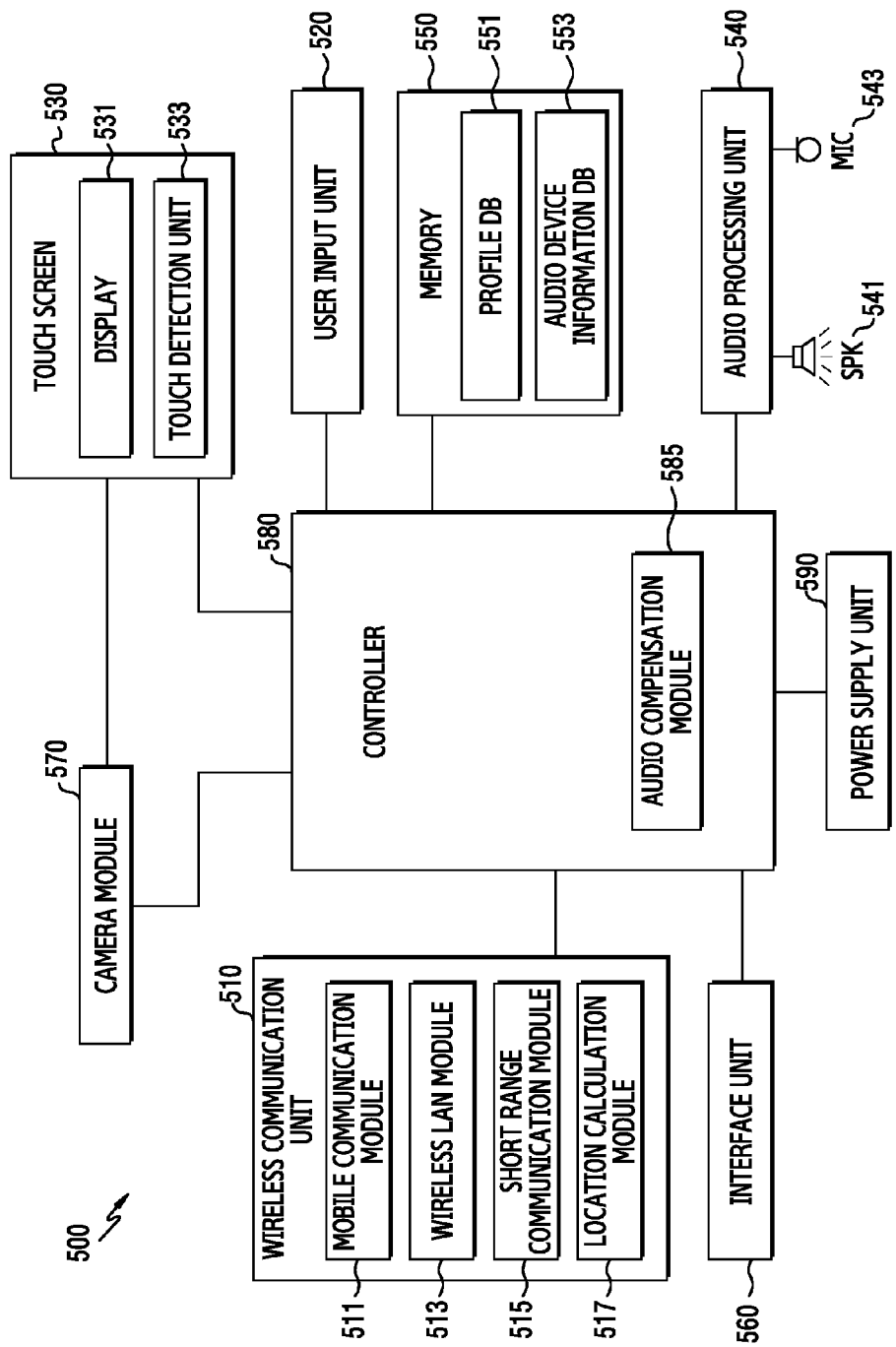
FIG. 5 is a block diagram illustrating a configuration of an electronic device according to various embodiments of the present disclosure.

FIG. 5 is a block diagram illustrating a configuration of an electronic device according to an embodiment of the present disclosure.

Referring to FIG. 5, an electronic device 500 according to various embodiments of the present disclosure include a wireless communication unit 510, a user input unit 520, a touch screen 530, an audio processing unit 540, a memory 550, an interface unit 560, a camera module 570, a controller 580, and a power supply unit 590. The electronic device 500 may include fewer or more elements than the elements of FIG. 5.

The wireless communication unit 510 may include a configuration identical to, or similar to, the communication module 220 of FIG. 2. The wireless communication unit 510 may include one or more modules which enable wireless communication between the electronic device 500 and an external electronic device. For example, the wireless communication unit 510 may include a mobile communication module 511, a wireless local area network (WLAN) module 513, a short range communication module 515, and a location calculation module 517. The wireless communication unit 510 may include a module (e.g. a short range communication module or a long range communication module) for communicating with an external electronic device.

The mobile communication module 511 may have a configuration identical to, or similar to, the cellular module 221 of FIG. 2. The mobile communication module 511 may transmit/receive a wireless signal to/from at least one of a base station, an external electronic device 104, and various servers (e.g. an integration server, a provider server, a content server, an Internet server, a cloud server, and the like) over a mobile communication network. The wireless signal may include a voice signal, a data signal, or various types of control signals. The mobile communication module 511 may transmit, in response to a user's request, various pieces of data required for an operation of the electronic device 500 to the external device 104, or the server 106.

The wireless LAN module 513 may have a configuration identical to, or similar to, the Wi-Fi module 223 of FIG. 2. The WLAN module 513 may establish wireless Internet access and a wireless LAN link with another electronic device 102 or the server 106. The WLAN module 513 may be mounted inside or outside the electronic device 500. Wireless Internet access technology may include Wi-Fi, wireless broadband (Wibro), world interoperability for microwave access (WiMax), high speed downlink packet access (HSDPA), millimeter wave (mmWave), and the like. The WLAN module 513 may be linked with another external electronic device, which is connected through the electronic device 500 and a network (e.g. a wireless Internet network), so as to transmit or receive various data of the electronic device 500 to or from an external electronic device 104 or a server 106. The WLAN module 513 may always maintain an on-state, or may be turned on based on settings of the electronic device 500 or a user input.

The short range communication module 515 may be a module for performing short range communication. The short range communication technology may include Bluetooth, Bluetooth low energy (BLE), radio frequency identification (RFID), infrared data association (IrDA), ultra-wideband (UWB), ZigBee, near field communication (NFC), etc. The short range communication module 515 may be linked with another external electronic device (e.g. the audio device 450), which is connected to the electronic device 500 through a network (e.g. a short range communication network), so as to transmit or receive various data of the electronic device 500 to or from the external electronic device. The short range communication module 515 may always maintain an on-state, or may be turned on based on settings of the electronic device 500 or a user input.

The location calculation module 517 may have a configuration identical to, or similar to, the GNSS module 227 of FIG. 2. The location calculation module 517 is a module for obtaining the location of the electronic device 500, and may include a global position system (GPS) module. The location calculation module 517 may measure the location of the electronic device 500 through a triangulation principle.

The user input unit 520 may have a configuration identical to, or similar to, the input device 250 of FIG. 2. The user input unit 520 may generate input data for controlling an operation of the electronic device 500 in response to a user input. The user input unit 520 may include at least one input device for detecting various inputs of a user. For example, the user input unit 520 may include a keypad, a dome switch, a physical button, a touch pad (resistive type/capacitive type), a jog & shuttle, and a sensor (e.g. the sensor module 240).

Some elements of the user input unit 520 may be implemented in the form of a button located outside the electronic device 500, or may be implemented in the form of a touch panel. The user input unit 520 may receive a user input for initiating an operation (e.g. a hearing test function for creating audio compensation information) of the electronic device 500 according to various embodiments of the present disclosure, and may generate an input signal according to the user input.

The touch screen 530 is an input/output device which may perform an input function and a display function together, and may include a display 531 (e.g. the display 160 or 260) and a touch detection unit 533. The touch screen 530 may provide an input/output interface between the electronic device 500 and the user, may transfer a touch input of the user to the electronic device 500, and may display an output from the electronic device 500 to the user. The touch screen 530 may display a visual output to the user. The visual output may be displayed in the form of text, graphics, videos, and a combination thereof.

According to various embodiments of the present disclosure, the display 531 may display (output) various pieces of information processed in the electronic device 500. For example, the display 531 may display a user interface (UI) or a graphical user interface (GUI) related to an operation which the electronic device 500 performs while being charged or an operation of performing data communication according to a USB interface connection. The display 531 may use various displays (e.g. the display 160). The display 531 may use a curved display.

According to various embodiments of the present disclosure, the display 531 may include a display control circuit (e.g. a display driver IC (DDI)) which provides an electrical signal (e.g. a multi high voltage level (MHVL) signal) to a display panel. The display control circuit is an element in the display 531, which provides a driving signal and data to the display 531 by using an electrical signal (e.g. an MHVL signal) so that an image (e.g. text, pictures, still images, dynamic images) is displayed on a screen, and may drive various types displays, such as LCD, PDP and OLED.

The touch detection unit 533 may have a configuration identical to, or similar to, the touch panel 252 of FIG. 2. The touch detection unit 533 may be mounted on the display 531 and may detect a user input which touches or is proximate to a surface of the touch screen 530. The user input may include a touch event or proximity event, which includes a single touch, a multi-touch, a hovering, and an air gesture. The touch detection unit 533 may receive a user input for initiating an operation related to the use of the electronic device 500 and may generate an input signal based on the user input.

The audio processing unit 540 may have a configuration identical to, or similar to, the audio module 280 of FIG. 2. The audio processing unit 540 may transmit an audio signal received from the controller 580 to a speaker (SPK) 541, and may transfer, to the controller 580, an audio signal, such as a voice, which is received from a microphone (MIC) 543. The audio processing unit 540 may convert voice/sound data into audible sound through the speaker 541 based on the control of the controller 580 and may output the audible sound and may convert an audio signal, such as a voice, which is received from the microphone 543 into a digital signal and transfer the digital signal to the controller 580. The audio processing unit 540 may output an audio signal on the basis of audio compensation information which is compensated according to the control of the controller 580.

The speaker 541 may output audio data that is received from the wireless communication unit 510 or stored in the memory 550. The speaker 541 may output an audio signal associated with various operations (functions) performed by the electronic device 500.

The microphone 543 may receive an input of an external audio signal and process the same as electrical voice data. Various noise reduction algorithms may be implemented in the microphone 543 or the controller 580 in order to remove noise from an external audio signal. The microphone 543 may receive an audio stream, such as a voice instruction (e.g. a voice instruction for initiating data communication).

The memory 550 (e.g. the memory 130 or 230) may store one or more programs that are executed by the controller 580, and may execute a function for temporarily storing input/output data. The input/output data may include, for example, a file or profile, such as a dynamic image, an image, a picture, and audio data. The memory 550 stores acquired data. Data acquired in real time may be stored in a temporary storage device, and data may be stored in a storage device for a long time.

According to various embodiments of the present disclosure, the memory 550 may include a profile DB 551 and audio device information DB 553.

According to various embodiments of the present disclosure, the profile DB 551 may indicate a database (DB) which includes a profile for compensating for an audio output characteristic according to each device identifier (e.g. ID) of an audio device. The profile DB 551 may have a device identifier of an audio device and a profile created through a hearing test performed by an interaction between the electronic device 500 and a user and stored memory 550. The profile DB 551 may store a frequency characteristic which reflects a device identifier (e.g. ID) of an audio device and the hearing characteristics of a user. The device identifier may use, for example, a MAC address of a device's Bluetooth chip, and the profile may be stored as a decibel (dB) value of a frequency according to each frequency band.

According to various embodiments of the present disclosure, the audio device information DB 553 may indicate a DB which includes a device identifier (e.g. ID) of an audio device or frequency information for compensating for an audio output characteristic according to the type of device. The audio device information DB 553 may have a device name (e.g. product name) of an audio device and the corresponding frequency information, stored in a database. The audio device information DB 553 may indicate a DB which stores a device identifier (e.g. ID) of an audio device and a unique frequency characteristic of the audio device as frequency information files, respectively, and manages the files in a database.

According to various embodiments of the present disclosure, the profile DB 551 and the audio device information DB 553 may be implemented in the controller 580 or an audio compensation module 585 of the controller 580.

The memory 550 may have a configuration identical or similar to the memory 230 of FIG. 2. According to various embodiments of the present disclosure, the memory 550 may store one or more programs and data, which are related to executing an audio compensation function. The audio compensation function converts an audio output characteristic in consideration of the characteristics of an audio device and the hearing characteristics of a user. The memory 550 may store one or more programs and data, which are related to executing a hearing test function. For example, the memory 550 may store instructions for executing the audio compensation function or the hearing test function. The memory 550 may store instructions which instruct the controller 580 (e.g. one or more processors) to acquire the identification information and/or characteristics of an audio device, at least partially based on a connection to the audio device, select pre-stored audio adaptation information, at least partially based on the acquired information and/or characteristics, change an audio signal, at least partially based on the audio adaptation information, and transmit the changed audio signal to the audio device.

According to various embodiments of the present disclosure, the instructions may include instructing the controller 580 to wirelessly receive identification information of an audio device from the audio device and instructing the controller 580 to acquire an impedance characteristic of the audio device and/or information on the audio device so as to determine the characteristics of the audio device, when the audio device is connected through the wired interface. The instructions may include instructing the controller 580 to provide selected audio to an audio device after a connection to the audio device, receive a user response to the audio through a user interface, and create audio adaptation information, at least partially based on the received response. The memory 550 may include one or more application modules (or software modules).

The interface unit 560 may have a configuration identical to, or similar to, the interface 270 of FIG. 2. The interface unit 560 may receive data or power from another external electronic device, and may transfer the data or power to each element included in the electronic device 500. The interface unit 560 may enable the data inside the electronic device 500 to be transmitted to another external electronic device. For example, the interface unit 560 may include a wired/wireless headphone port, an external charging device port, a wired/wireless data port, a memory card port, an input/output port, a video input/output port, an earphone port, etc.

The camera module 570 (e.g. the camera module 291) supports a photographing function of the electronic device 500. The camera module 570 may photograph an object under control of the controller 580, and transfer the photographed data (e.g. images) to the display 531 and the controller 580.

The controller 580 may control overall operations of the electronic device 500. According to various embodiments of the present disclosure, the controller 580 may have a configuration identical to, or similar to, the processor 210 of FIG. 2. The controller 580 may detect a connection to an audio device, and may process a hearing test in response to the connected audio device or converting and outputting audio characteristics on the basis of audio compensation information.

According to various embodiments of the present disclosure, the controller 580 may include the audio compensation module 585. The audio compensation module 585 may detect an audio device connection and determine whether to perform a hearing test or perform audio output characteristic conversion. On the basis of a result of the determination, the audio compensation module 585 may process an operation related to the hearing test or process an operation related to converting the audio output characteristic to output audio. The audio compensation module 585 may include a memory including at least one DB corresponding to the profile DB 551 and the audio device information DB 553. An operation of the audio compensation module 585 will be described in detail with reference to the drawings.

The controller 580 may include one or more processors for controlling an operation of the electronic device 500. The controller 580 may control operations of hardware modules, such as the audio processing unit 540, the interface unit 560, and the display 531. The control operation of the controller 580 will be described in detail with reference to the drawings.

According to various embodiments of the present disclosure, the controller 580 may be linked with software modules stored in the memory 550 so as to perform an audio compensation and hearing test operation based on an audio device characteristic of the electronic device 500. The controller 580 may be embodied as one or more processors that are configured to control an operation of the electronic device 500 by executing one or more programs stored in the memory 550.

The power supply unit 590 may receive external power or internal power based on the control of the controller 580 and supply power required for the operation of each element. According to various embodiments of the present disclosure, the power supply unit 590 may provide, or cut off, power supply to the display 531, the camera module 570, and the like on the basis of a control of the controller 580.

Various embodiments of the present disclosure may be implemented in a computer or a similar non-transitory device-readable recording medium through software, hardware or a combination thereof.

Hereinafter, an operation of processing an audio output will be described according to various embodiments of the present disclosure with reference to FIGS. 6, 7, and 8. A description of FIGS. 6, 7, and 8 will be made by using an example in which the audio compensation module 585 includes at least one DB corresponding to the profile DB 551 and the audio device information DB 553. However, the present disclosure is not limited to this embodiment. As in the above description made with reference to FIG. 5, the audio compensation module 585 may receive relevant information stored in the profile DB 551 and audio device information DB 553 of the memory 550 so as to process an audio output.

Figure 6:
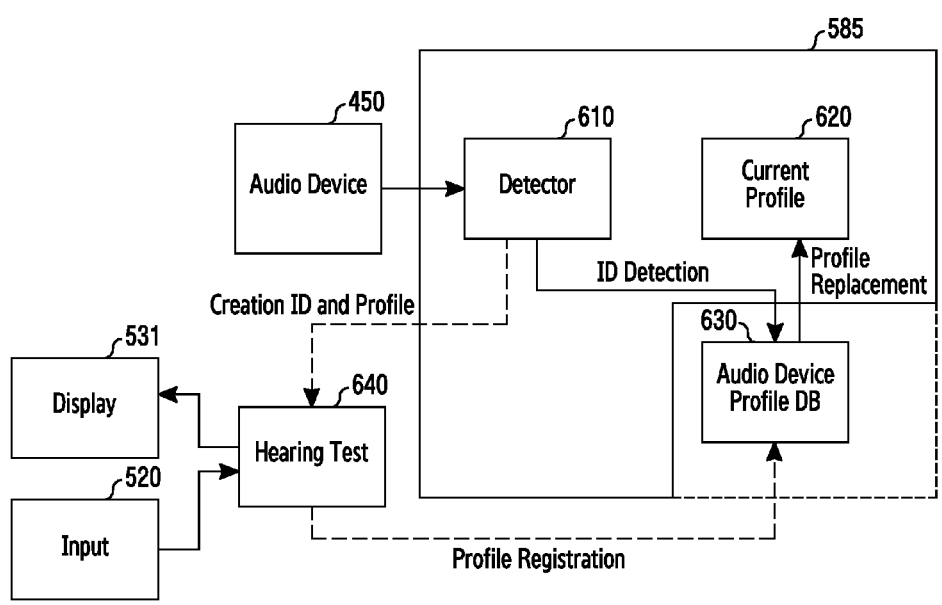
FIG. 6 illustrates processing an audio output in an electronic device, according to an embodiment of the present disclosure.

FIG. 6 illustrates processing an audio output in an electronic device according to various embodiments of the present disclosure.

Referring to FIG. 6, FIG. 6 illustrates an operation of the controller 580 (e.g. the audio compensation module 585) when the audio device 450, which is connected to the electronic device 500, is an active audio device. According to various embodiments of the present disclosure, the active audio device is configured to have an internal digital circuit which may establish wireless communication (e.g. Bluetooth) with the electronic device 500 and may include an audio output device having a device identifier (e.g. ID).

As illustrated in FIG. 6, when the audio device 450 is connected, the electronic device 500 may detect (perform ID detection) a device identifier (e.g. ID) of the audio device 450 through a detector 610. The detector 610 may detect whether the device identifier of the audio device 450 is a device identifier registered in a profile DB 630 (e.g. an audio device hearing profile DB) of the electronic device 500. The profile DB 630 may be implemented and used inside the audio compensation module 585, or may be implemented (e.g. according to FIG. 5) and used outside (e.g. the memory 550) the audio compensation module. Table 1 below shows an example of the profile DB 630 in which a profile for each audio device is registered.

TABLE 1

| ID (Device MAC Address) | Profile |
|---|---|
| 00:12:a1:67:37:73 | [25, 20, 20, 15, 20, 30, 15, 30, 25, 10, 15, 20] |
| 08:b1:37:21:85:a1 | [15, 25, 20, 20, 25, 35, 20, 25, 15, 15, 20, 25] |
| 05:12:a1:38:58:12 | [25, 20, 20, 15, 20, 30, 15, 30, 25, 10, 15, 20] |
| 00:14:a1:38:68:42 | [25, 15, 20, 15, 20, 30, 15, 30, 25, 15, 15, 20] |

According to various embodiments of the present disclosure, the profile DB 630 may include a database for storing a frequency characteristic which reflects a device identifier (e.g. ID) of the audio device 450 and the hearing characteristics of a user. The device identifier may use, for example, a MAC address of Bluetooth, and the profile may store a decibel (dB) value of a frequency according to each frequency band. The profile DB 630 may be created by generating a database from a device identifier of an audio device, and the test which has been completed through a hearing test 640. The electronic device 500 may include a measurement device (e.g. hearing test unit) for the hearing test 640 and may perform measurements by software processing.

When it is determined that the connected audio device 450 is an audio device registered in the profile DB 630, for example, when there is a device identifier of the audio device 450 existing in the profile DB 630, the electronic device 500 may change a current profile 620 to the relevant profile registered in the profile DB 630.

When it is determined that the connected audio device 450 is not an audio device registered in the profile DB 630, for example, when there is no device identifier of the audio device 450 in the profile DB 630, the electronic device 500 may perform the hearing test 640 for creating a profile related to the connected audio device 450.

According to an embodiment of the present disclosure, the electronic device 500 may provide a user interface for a hearing test through the display 531 and may perform the hearing test 640 through user interaction using the user interface. The electronic device 500 may reflect (e.g. convolute) a user's hearing characteristics corresponding to the frequency characteristic of the audio device 450 connected in response to the user input 520 and then store the result (e.g. a profile) of the reflection in the profile DB 630. In other words, the electronic device 500 may store a result reflected after a user hearing test is performed according to each audio device 450 as a profile of each audio device 450. Thereafter, when the audio device 450 accesses the electronic device 500, the electronic device 500 may automatically apply a profile related to the connected audio device 450 to the current profile 620 of the current user and output audio as a frequency which reflects the user hearing characteristics related to the connected audio device 450. The profile DB 630 may store profiles related to multiple users of the audio device 450.

Figure 7:
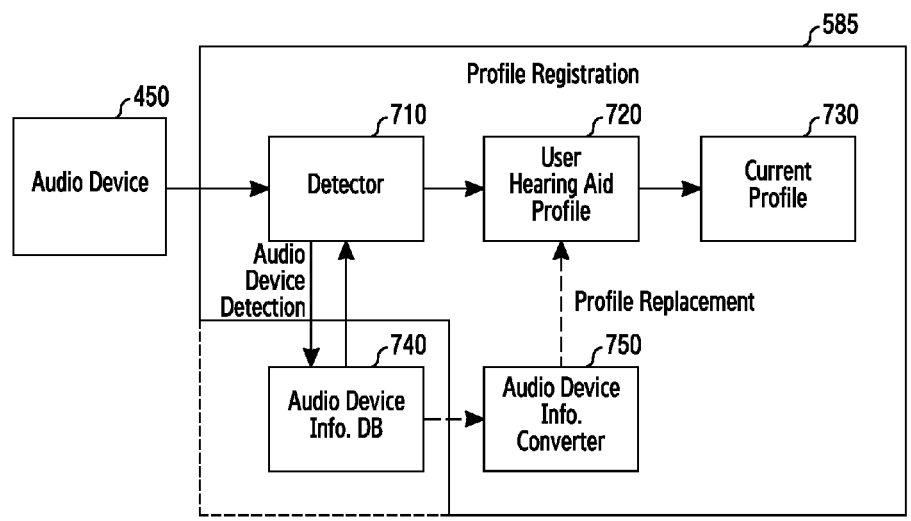
FIG. 7 illustrates processing an audio output in an electronic device, according to another embodiment of the present disclosure.

FIG. 7 illustrates processing an audio output in an electronic device according to another embodiment of the present disclosure.

Referring to FIG. 7, FIG. 7 illustrates an operation of the controller 580 (e.g. the audio compensation module 585) when the audio device 450, which is connected to the electronic device 500, is an active audio device. According to various embodiments of the present disclosure, the active audio device is configured to have an internal digital circuit which may establish wireless communication (e.g. Bluetooth) with the electronic device 500 and may include a device identifier (e.g. ID).

As illustrated in FIG. 7, when the audio device 450 is connected, the electronic device 500 may detect a device identifier (e.g. ID) of the connected audio device 450 through a detector 710. According to various embodiments of the present disclosure, the detector 710 may determine frequency information corresponding to the detected device identifier in an audio device information DB 740 of the electronic device 500. The audio device information DB 740 may be implemented and used inside the audio compensation module 585, or may be implemented (e.g. according to FIG. 5) and used outside (e.g. the memory 550) the audio compensation module. The audio device information DB 740 may store a database including a device name (e.g. product name) and frequency information of the connected audio device 450. Table 2 below shows an example of the audio device information DB 740.

TABLE 2

| Active Audio Acc. | Frequency Info. |
|---|---|
| 00:12:a1:67:37:73 | [5, 20, 10, 15, 20, 30, 15, 30, 25, 10, 15, 20] |
| 08:b1:37:21:85:a1 | [1, 5, 0, 20, 25, 35, 0, 25, 15, 15, 0, 5] |

TABLE 2-continued

| Active Audio Acc. | Frequency Info. |
|---|---|
| 05:12:a1:38:58:12 | [5, 0, 0, 5, 0, 0, 5, 10, 15, 0, 15, 20] |
| 06:14:a1:38:58:11 | [5, 10, 0, 5, 0, 10, 5, 10, 15, 0, 15, 20] |

According to various embodiments of the present disclosure, the audio device information DB 740 may indicate a DB which stores a device identifier (e.g. ID) of the audio device 450 or frequency information for compensating for an audio output characteristic according to the type of device. The audio device information DB 740 may indicate a DB which stores a device identifier (e.g. ID) of an audio device and a unique frequency characteristic of the audio device as frequency information files, respectively, and renders the files into a database to manage the files.

The electronic device 500 may determine whether the frequency information of the connected audio device 450 corresponds to currently established frequency information. When the frequency information of the connected audio device 450 corresponds to the currently established frequency information, the electronic device 500 may create a user hearing aid profile 720 on the basis of the corresponding frequency information. For example, the electronic device 500 may combine the currently established frequency information and a user's pre-established hearing characteristics to create an optimized profile in which the frequency characteristic of the connected audio device 450 and the user's hearing characteristics are considered and compensated for. The electronic device 500 may change a current profile 730 to the created profile.

When the frequency information of the connected audio device 450 does not correspond to the currently established frequency information, the electronic device 500 may search for the frequency information of the audio device 450 from among frequency information according to each audio device registered in the audio device information DB 740. The electronic device 500 may search for the device identifier of the audio device 450 in the audio device information DB 740 or may directly search for the corresponding frequency information.

According to various embodiments of the present disclosure, when the audio device information DB 740, includes the device identifier of the audio device 450 and the corresponding frequency information, the electronic device 500 may change the currently established frequency information to the frequency information in the audio device information converter 750. For example, the electronic device 500 may replace the currently established frequency information with frequency information of the currently connected audio device 450, which is stored in the audio device information DB 740. The electronic device 500 may create the user hearing aid profile 720 on the basis of the replaced frequency information. For example, the electronic device 500 may combine the changed frequency information and a user's pre-established hearing characteristics to create an optimized profile in which the frequency characteristic of the connected audio device 450 and the user's hearing characteristics are considered and compensated for. The electronic device 500 may change the current profile 730 to the created profile.

According to various embodiments of the present disclosure, when the device identifier of the audio device 450 and the corresponding frequency information are not in the audio device information DB 740, the electronic device 500 may update (e.g. register) the audio device information DB 740.

The electronic device 500 may be connected to (may communicate with) a server which provides audio device information, and may receive the audio device information from the server through wireless communication (e.g. Internet and the like) to update the audio device information DB 740. A user may directly input a value corresponding to the audio device information, and the electronic device 500 may update the audio device information DB 740 on the basis of the value, which is input by the user, corresponding to the audio device information. The electronic device 500 may directly download frequency information recorded in an audio device, which is connected through Bluetooth and the like, from the audio device to update the audio device information DB 740.

Figure 8:
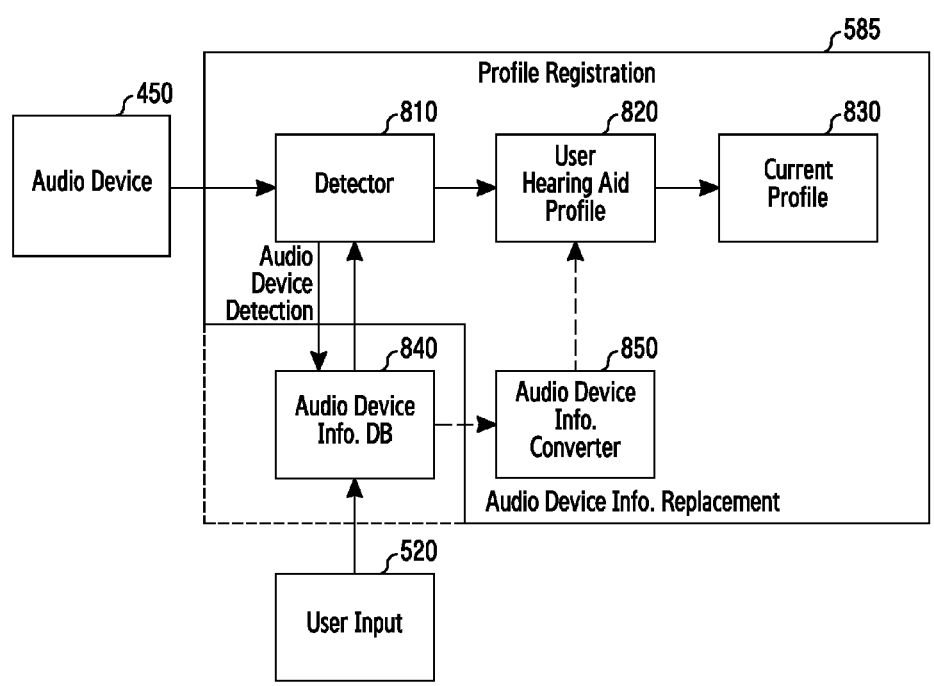
FIG. 8 illustrates processing an audio output in an electronic device, according to another embodiment of the present disclosure.

FIG. 8 illustrates processing an audio output in an electronic device according to another embodiment of the present disclosure.

Referring to FIG. 8, FIG. 8 illustrates of an operation of the controller 580 (e.g. the audio compensation module 585) when the audio device 450, which is connected to the electronic device 500, is a passive audio device. The passive audio device may establish wired communication (e.g. connector connection) with the electronic device 500, may not have an internal digital circuit, and may include audio output devices having different resistances (or impedances).

As illustrated in FIG. 8, when the audio device 450 is connected, the electronic device 500 may determine the resistance of the audio device 450 through impedance detection in a detector 810. The electronic device 500 may determine, on the basis of the determined resistance, frequency information related to the currently connected audio device 450. According to various embodiments of the present disclosure, the frequency information related to the audio device 450 may be determined on the basis of a mapping table in which frequency information is mapped according to various resistances of the passive audio device. The audio device 450 may utilize a resistance of an existing 3-pole or 4-pole ear jack and may also utilize any one pole among 3 poles (or terminals) or 4 poles (or terminals) as a pole for transferring an ID for identification of an audio device. The audio device 450 having 5 poles or more may utilize any one terminal of the 5 poles as a pole for transferring an ID for identification of an audio device.

According to various embodiments of the present disclosure, the detector 810 may determine frequency information corresponding to the currently connected audio device 450 in an audio device information DB 840 of the electronic device 500. The audio device information DB 840 may be implemented and used inside the audio compensation module 585, or may be implemented (e.g. in the form of FIG. 5) and used outside (e.g. the memory 550) the audio compensation module. The audio device information DB 840 may store a database including a device name (e.g. product name) and frequency information of the connected audio device 450. Table 3 below shows an example of the audio device information DB 840.

TABLE 3

| Passive Audio Acc. | Frequency Info. |
|---|---|
| MDR-1RBT MK2 | [5, 0, 10, 10, 20, 30, 15, 30, 25, 20, 25, 20] |
| PX200-II | [2, 5, 0, 20, 25, 30, 10, 25, 15, 15, 0, 5] |
| MOMENTUM | [5, 5, 0, 5, 0, 0, 5, 10, 15, 0, 15, 20] |
| AKG K450 | [5, 5, 5, 0, 5, 5, 0, 5, 15, 15, 20, 25] |
| AKG K560 | [5, 5, 5, 0, 5, 5, 0, 15, 15, 15, 25, 25] |

According to various embodiments of the present disclosure, the audio device information DB 840 may indicate a DB which stores a device identifier (e.g. a resistance value) of the audio device 450 or frequency information for compensating for an audio output characteristic according to the type (e.g. a device name) of device. The audio device information DB 840 may indicate a DB which stores a device identifier (e.g. resistance value) of an audio device and a unique frequency characteristic of the audio device as frequency information files, respectively, and renders the files into a database to manage the files.

The electronic device 500 may determine whether the frequency information of the connected audio device 450 corresponds to currently established frequency information. When the frequency information of the connected audio device 450 corresponds to the currently established frequency information, the electronic device 500 may create a user hearing aid profile 820 on the basis of the corresponding frequency information. For example, the electronic device 500 may combine the currently established frequency information and a user's pre-established hearing characteristics to create an optimized profile in which the frequency characteristic of the connected audio device 450 and the user's hearing characteristics are considered and compensated for. The electronic device 500 may change a current profile 830 to the created profile.

When the frequency information of the connected audio device 450 does not correspond to the currently established frequency information, the electronic device 500 may provide, to the user, frequency information according to each audio device registered in the audio device information DB 840. For example, the electronic device 500 may display a list of audio devices registered in the audio device information DB 840 through a user interface by using the display 531. The electronic device 500 may receive the user input 520 which selects a particular audio device (e.g. a model corresponding to the currently connected audio device) from the user through the user interface. The user may select an item (e.g. device name) corresponding to the currently connected audio device 450 from the list provided through the user interface. In the case of a passive audio device, the user may manually select frequency information because there is no device identifier (e.g. ID). The operation of the electronic device is not limited thereto, and the electronic device may be operated to detect each resistance included in the passive audio device as a unique device identifier and then automatically select frequency information.

When the frequency information of the audio device 450 is selected, the electronic device 500 may change the currently established frequency information to the selected frequency information through an audio device information converter 850. For example, the electronic device 500 may change the currently established frequency information to frequency information of the currently connected audio device 450, which is selected from the audio device information DB 840. The electronic device 500 may create the user hearing aid profile 820 on the basis of the changed frequency information. For example, the electronic device 500 may combine the changed frequency information and a user's pre-established hearing characteristics to create an optimized profile in which the frequency characteristic of the connected audio device 450 and the user's hearing characteristics are considered and compensated for. The electronic device 500 may change the current profile 830 to the created profile.

Figures 9A, 9B:
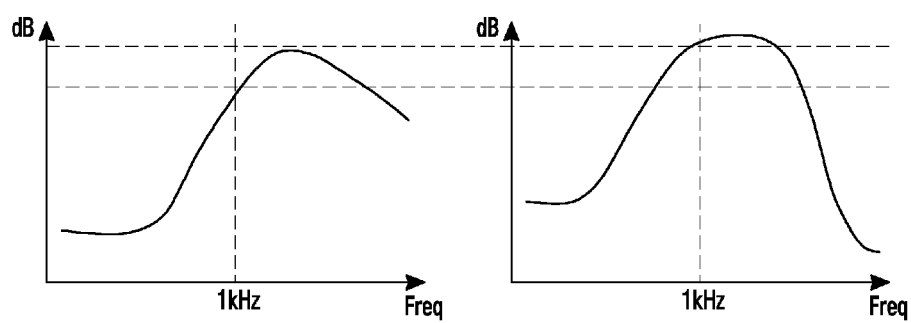
FIG. 9A illustrates the result of a change in an audio output characteristic in an electronic device according to an embodiment of the present disclosure.
FIG. 9B illustrates the result of a change in an audio output characteristic in an electronic device according to another embodiment of the present disclosure.

FIG. 9A illustrates the result of a change in an audio output characteristic in an electronic device according to an embodiment of the present disclosure.

FIG. 9B illustrates the result of a change in an audio output characteristic in an electronic device according to another embodiment of the present disclosure.

Referring to FIGS. 9A and 9B, an audio device used while being connected to the electronic device 500 may include a wired audio device (e.g. a wired earphone, a wired headphone) and a wireless audio device (e.g. a wireless earphone, a wireless headphone). The wired audio device (e.g. a passive audio device) may have a difference in sound quality and characteristics on the basis of various resistances (e.g. 16 ohm, 32 ohm, 300 ohm, etc.). Further, the wireless audio device (e.g. an active audio device) may also show various characteristics according to the type or the manufacturer thereof. For example, FIG. 9A shows an example of the frequency characteristic of a first audio device and FIG. 9B shows an example of the frequency characteristic of a second audio device. In a frequency comparison in the 1 KHz band, a volume difference may be generated according to each audio device, causing a change which a user may hear.

Figures 10A, 10B:
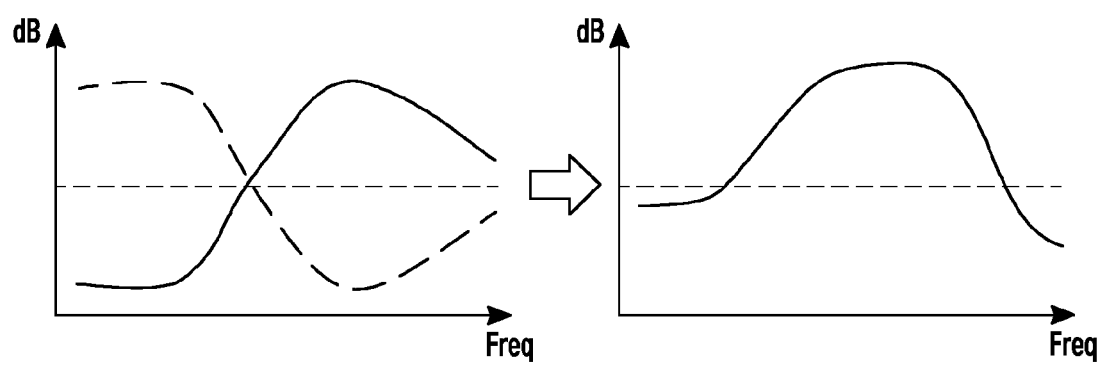
FIG. 10A illustrates the result of a change in an audio output characteristic in an electronic device according to another embodiment of the present disclosure.
FIG. 10B illustrates the result of a change in an audio output characteristic in an electronic device according to another embodiment of the present disclosure.

FIG. 10A illustrates the result of a change in an audio output characteristic in an electronic device according to another embodiment of the present disclosure.

FIG. 10B illustrates the result of a change in an audio output characteristic in an electronic device according to another embodiment of the present disclosure.

Referring to FIGS. 10A and 10B, according to various embodiments of the present disclosure, the characteristics of an audio device may be changed on the basis of a user's hearing characteristics. For example, as illustrated in FIG. 10A, it may possible to create an anti-phase frequency (dotted line) (e.g. compensation frequency) of a frequency (solid line) of a preregistered audio device and make a frequency converge to zero by multiplying a basic frequency and the compensation frequency. Thereafter, new frequency information may be created through multiplying the frequency information of the connected audio device by the created frequency information and mapping and storing the result as a characteristic of the audio device. In other words, the frequency characteristic of the audio device may be changed in consideration of the user's hearing characteristics. Therefore, the user may configure sound quality optimized to the user's hearing characteristics according to each audio device, and, when the user makes a call or listens to audio of music or video while an audio device is connected, the user may listen to audio having an optimized sound quality.

According to various embodiments of the present disclosure, an electronic device may include a user interface, a wired or wireless interface configured to establish a connection to an audio device, a memory, and one or more processors that are electrically connected to the user interface, the memory, and the wired or wireless interface, wherein the memory, at the time of execution, stores instructions that instruct the one or more processors to, acquire identification information and/or characteristics of the audio device, at least partially based on the connection to the audio device, select pre-stored audio adaptation information, at least partially based on the acquired information and/or characteristics, change an audio signal, at least partially based on the audio adaptation information, and transmit the changed audio signal to the audio device.

According to various embodiments of the present disclosure, the electronic device store instructions which may include instructing the processors to wireless receive the identification information of the audio device from the audio device. The instructions may include instructing the processors to acquire an impedance characteristic of the audio device and/or audio device information to determine the characteristics of the audio device, when the audio device is connected to the wired interface. The instructions may include instructing the processors to provide a selected audio to the audio device after a connection to the audio device, receive a user response to the audio through the user interface, and create the audio adaptation information, at least partially based on the received response.

As described above, according to various embodiments of the present disclosure, the electronic device includes a communication interface configured to establish a connection to an audio device, a memory, and one or more processors that are electrically connected to the memory and the communication interface, wherein the one or more processors perform determining audio adaptation information related to the audio device in response to the audio device connection, correcting an audio output corresponding to the audio device on the basis of the audio adaptation information when the audio adaption information has been registered, and updating, when the audio adaption information has not been registered, the audio adaptation information related to the audio device and correcting an audio output corresponding to the characteristics of the audio device on the basis of the updated audio adaptation information.

According to various embodiments of the present disclosure, an electronic device includes a wired or wireless interface configured to establish a connection to an audio device, a memory, and one or more processors that are electrically connected to the memory and the wired or wireless interface, wherein the memory, at the time of execution, stores instructions that instruct the one or more processors to, establish audio adaptation information on the basis of a frequency characteristic of the audio device and a user's hearing characteristics, detect a connection of the audio device, determine audio adaptation information related to a connected audio device, convert a currently established audio output characteristic to an audio output characteristic corresponding to the connected audio device on the basis of the determined audio adaptation information, and process an audio output on the basis of the converted audio output characteristic.

According to various embodiments of the present disclosure, the audio adaptation information may be configured to include a profile for compensating for an audio output characteristic according to each audio device, or frequency information of the audio device. The memory may be configured to include a profile DB which stores device information of the audio device and a profile, and an audio device information DB which stores device information and frequency information of the audio device.

According to various embodiments of the present disclosure, the one or more processors may be configured to combine a unique frequency characteristic of the audio device and a user's hearing characteristics to establish audio adaption information.

According to various embodiments of the present disclosure, the one or more processors may be configured to determine whether to perform, in response to the detection of the audio device connection, a hearing test or perform audio output characteristic conversion based on pre-established audio adaptation information.

According to various embodiments of the present disclosure, the one or more processors may be configured to provide a user interface when determining to perform the hearing test, perform a hearing test which combines the frequency characteristic of a connected audio device and a user's hearing characteristics according to an interaction with the user based on the user interface, and create a profile related to the connected audio device on the basis of the result of the hearing test. The one or more processors may be configured to convert a currently established profile to the created profile.

According to various embodiments of the present disclosure, the one or more processors may be configured to determine the frequency information of a connected audio device in response to the audio device connection, combine currently established frequency information and a user's hearing characteristics when the frequency information of the audio device corresponds to the currently established frequency information, automatically search for the frequency information of the connected audio device in the audio device information DB when the frequency information of the audio device does not correspond to the currently established frequency information, convert the currently established frequency information to the stored frequency information; and combine the converted frequency information and the user's hearing characteristics.

According to various embodiments of the present disclosure, the one or more processors may be configured to provide a list of audio devices with reference to the audio device information DB when the frequency information of the audio device does not correspond to the currently established frequency information, and convert the currently established frequency information to frequency information manually selected by the user on the basis of the list.

According to various embodiments of the present disclosure, the one or more processors may be configured to create a profile by the combination of the converted frequency information and the user's hearing characteristics and convert a current profile currently established in the electronic device to the created profile.

According to various embodiments of the present disclosure, the one or more processors may be configured to perform detecting an audio device connection, determining audio adaptation information related to the audio device in response to the audio device connection, correcting an audio output corresponding to the audio device on the basis of the audio adaptation information when the audio adaption information has been registered, updating the audio adaptation information related to the audio device when the audio adaption information has not been registered, and correcting an audio output corresponding to a characteristic of the audio device on the basis of the updated audio adaptation information.

According to various embodiments of the present disclosure, the one or more processors, at the time of updating, may be configured to perform providing a user interface when determining to perform the hearing test, carrying out the hearing test which combines the characteristics of a connected audio device and a user's hearing characteristics according to an interaction with the user based on the user interface, and creating a profile related to the connected audio device on the basis of the result of the hearing test.

According to various embodiments of the present disclosure, the one or more processors, at the time of updating, may be configured to perform determining the frequency information of a connected audio device in response to an audio device connection, combining currently established frequency information and a user's hearing characteristics when the frequency information of the audio device corresponds to the currently established frequency information, automatically searching for frequency information of the connected audio device in the audio device information DB when the frequency information of the audio device does not correspond to the currently established frequency information, converting the currently established frequency information to the stored frequency information; and combining the converted frequency information and the user's hearing characteristics.

According to various embodiments of the present disclosure, the one or more processors, at the time of updating, may be configured to perform providing a list of audio devices with reference to the audio device information DB when the frequency information of the audio device does not correspond to the currently established frequency information, converting the currently established frequency information to frequency information manually selected by the user on the basis of the list, and combining the converted frequency information and the user's hearing characteristics.

According to various embodiments of the present disclosure, the one or more processors may be configured to perform creating a profile by the combination of the converted frequency information and the user's hearing characteristics and converting a current profile currently established in the electronic device to the created profile, and converting and outputting audio on the basis of the characteristics of the converted profile.

Figure 11:
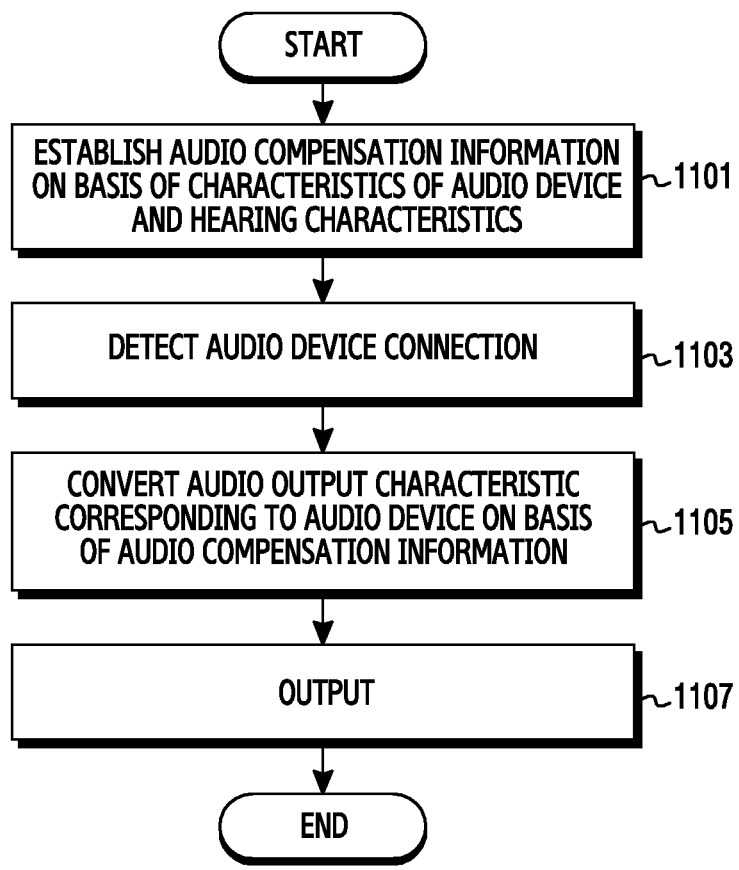
FIG. 11 is a flowchart illustrating a method for outputting audio in an electronic device according to an embodiment of the present disclosure.

FIG. 11 is a flowchart illustrating a method for outputting audio in an electronic device according to various embodiments of the present disclosure.

Referring to FIG. 11, in step 1101, the controller 580 establishes audio compensation information on the basis of the characteristics (e.g. frequency characteristic) of an audio device and a user's hearing characteristics. For example, the user may perform compensation (e.g. hearing test for a connected audio device) according to a user's hearing characteristics with respect to various audio devices by using the electronic device 500, and the electronic device 500 may create audio compensation information (e.g. a profile) related to the audio device on the basis of the result of the hearing test. The audio compensation information according to each audio device may be managed as a DB, as described above.

In step 1103, the controller 580 detects the connection of the audio device. For example, the user may connect an audio device, to the electronic device 500. On the basis of the type of audio device, the user may connect the audio device to the electronic device 500 through wireless communication (e.g. Bluetooth) or may connect the audio device to the electronic device 500 through wired communication (e.g. connector).

In step 1105, the controller 580 changes an audio output characteristic to correspond to the audio device on the basis of pre-established audio compensation information corresponding to the audio device. The controller 580 may change a currently established audio output characteristic (e.g. a current profile) to an audio output characteristic corresponding to the connected audio device in response to the detection of the audio device connection.

In step 1107, the controller 580 outputs audio on the basis of the changed audio output characteristic and transfers the output audio to the connected audio device.

Figure 12:
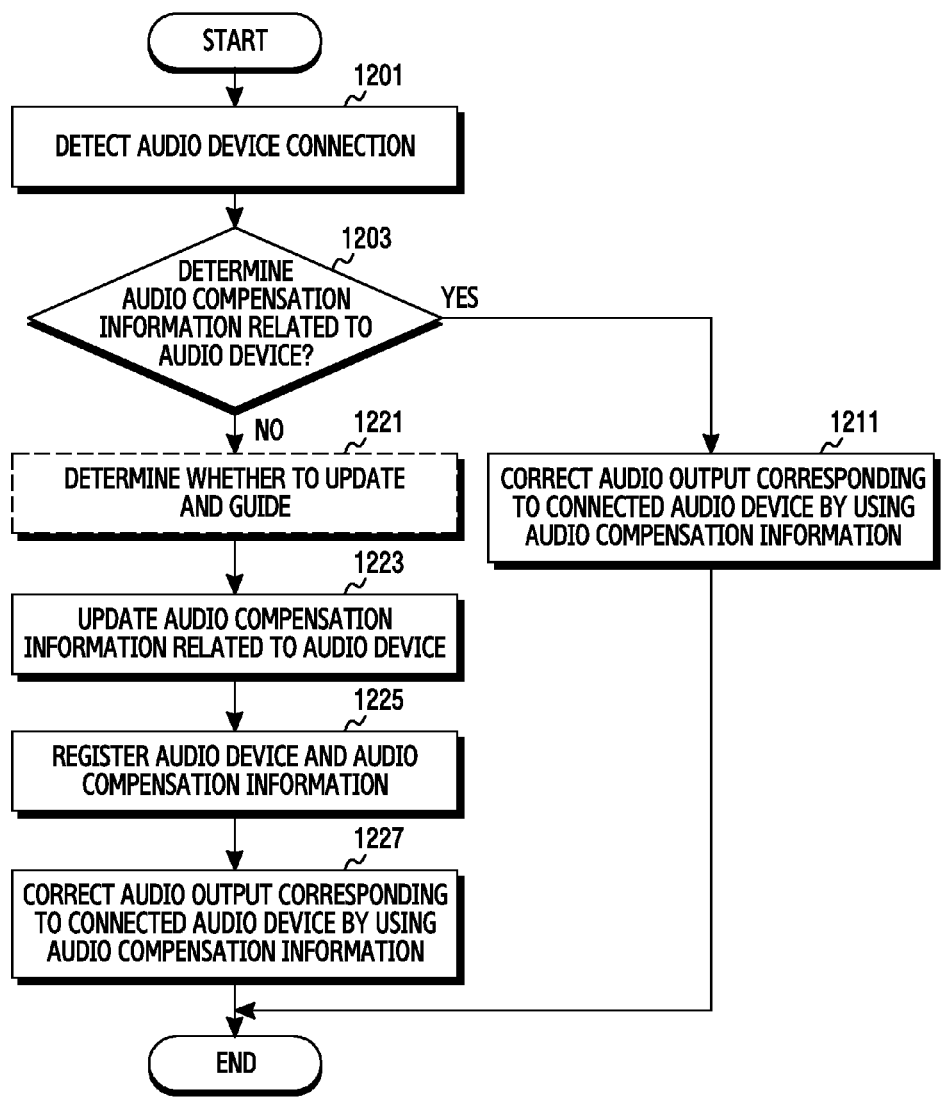
FIG. 12 is a flowchart illustrating a method for correcting an audio output in an electronic device according to an embodiment of the present disclosure.

FIG. 12 is a flowchart illustrating a method for correcting an audio output in an electronic device according to various embodiments of the present disclosure.

Referring to FIG. 12, in step 1201, the controller 580 may detect the connection of an audio device.

In step 1203, the controller 580 determines audio compensation information related to a connected audio device. For example, the controller 580 may determine whether there is audio compensation information (e.g. a profile, frequency information) related to the connected audio device in a pre-established DB (e.g. a profile DB, an audio device information DB).

When the controller 580 determines, in step 1203, that there is audio compensation information related to the audio device, the controller 580 performs, in step 1211, audio output correction corresponding to a currently connected audio device by using the audio compensation information.

When the controller 580 does not determine, in step 1203, that there is audio compensation information related to the audio device, the controller 580 determines, in step 1221, whether to update the audio compensation information related to the connected audio device and provide a guide for the updating. For example, the controller 580 may determine whether audio is established, and may output a relevant user interface in response to a user selection (e.g. approval/rejection). Step 1221 may be excluded and the method may immediately proceed to step 1223 to perform updating, depending on the setting of the electronic device 500.

In step 1223, the controller 580 updates the audio compensation information related to the audio device. For example, the controller 580 may output a user interface, as in FIG. 17 described below, and may perform a hearing test in response to a user input, which is input through the user interface, and determine the result (e.g. audio compensation information) of the hearing test.

In step 1225, the controller 580 registers information (e.g. device information, device identifier) on a currently connected audio device and the audio compensation information. For example, the controller 580 may update the information on the audio device and relevant audio compensation information in a pre-established DB.

In step 1227, the controller 580 performs audio output correction corresponding to the currently connected audio device by using the audio compensation information.

Figure 13:
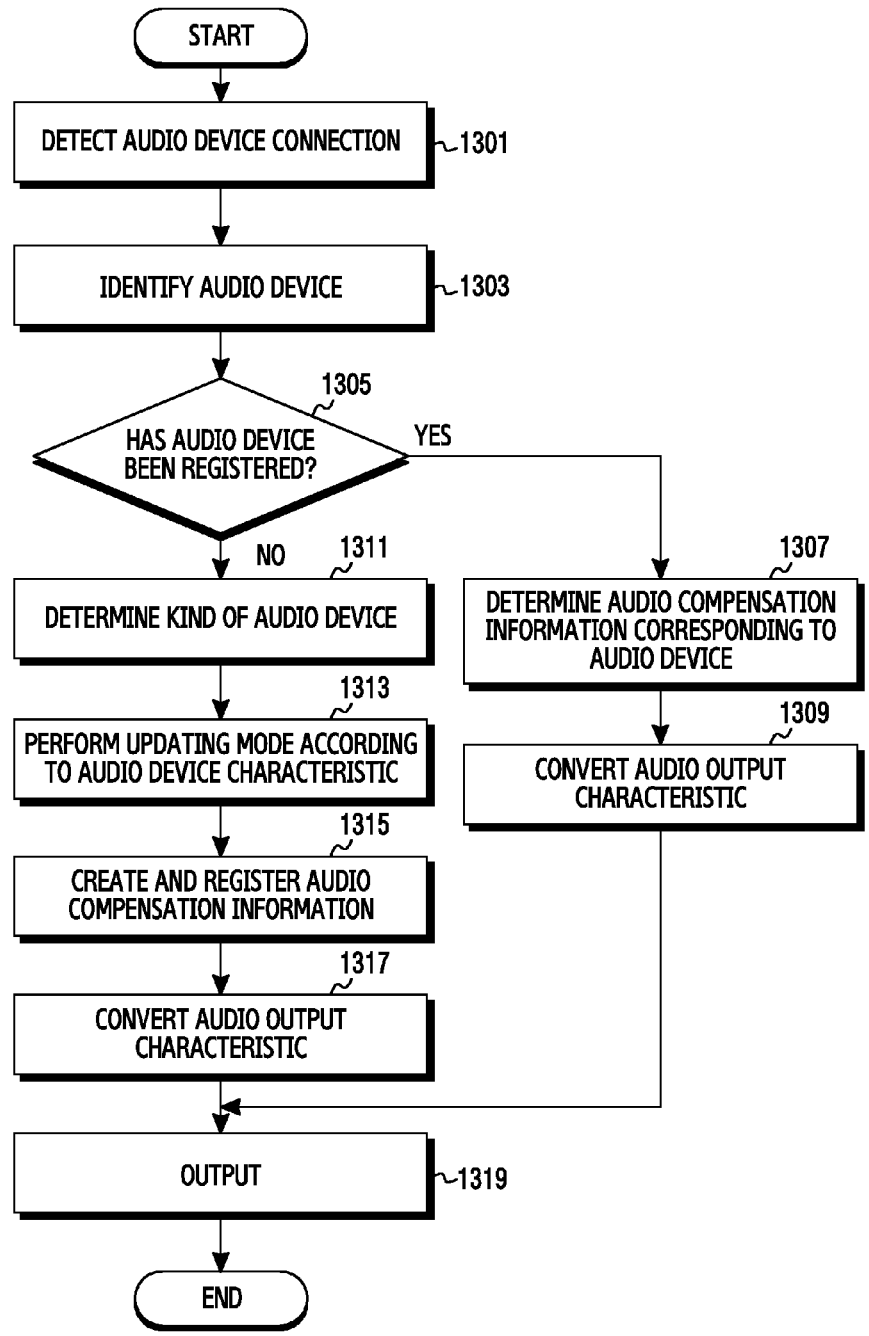
FIG. 13 is a flowchart illustrating a method for processing an audio output in an electronic device according to an embodiment of the present disclosure.

FIG. 13 is a flowchart illustrating processing an audio output in an electronic device according to various embodiments of the present disclosure.

Referring to FIG. 13, in step 1301, the controller 580 detects the connection of an audio device.

In steps 1303 and 1305, the controller 580 identifies an audio device and determines whether a currently connected audio device corresponds to a pre-registered audio device. For example, the controller 580 may detect a device identifier (e.g. ID, resistance value) of the connected audio device in response to the detection of the audio device connection, and may determine whether the detected device identifier is registered in the pre-established DB.

When the controller 580 determines, in step 1305, that the connected audio device is a registered audio device ("Yes" in step 1305), the controller 580 determines, in step 1307, audio compensation information corresponding to the audio device.

In step 1309, the controller 580 converts an audio output characteristic related to the currently connected audio device on the basis of audio compensation information according to the result of the determination.

When the controller 580 determines, in step 1305, that the connected audio device is an unregistered audio device ("No" in step 1305), the controller 580 determines the type of connected audio device in step 1311. For example, the controller 580 may determine whether the connected audio device is an active audio device or a passive audio device. In addition, the controller 580 may determine whether the connected audio device is wirelessly connected or is wired connected. Further, when it is determined that the connected audio device is an active audio device, the controller 580 may determine whether the device identifier (e.g. ID) of the audio device is registered in a profile DB or the device information (e.g. frequency information) of the audio device is registered in an audio device information DB.

In step 1313, the controller 580 determines an updating mode corresponding to the determined type of audio device and performs the determined updating mode. The controller 580 may provide a user interface for a hearing test, as in FIG. 17 described below, and may perform the updating mode, such as performing the hearing test by interaction with a user based on the user interface. Further, the controller 580 may search the audio device information DB for frequency information of the currently connected audio device, and may perform the updating mode, such as combining a user's hearing characteristics with the stored frequency information.

According to various embodiments of the present disclosure, when the device identifier of the audio device and the corresponding frequency information are not in the audio device information DB, the controller 580 may update (e.g. register) the audio device information DB. The controller 580 may be connected to (may communicate with) a server which provides audio device information, and may receive the audio device information from the server through wireless communication (e.g. Internet and the like) to update the audio device information DB. The user may directly input a value corresponding to the audio device information, and the controller 580 may update the audio device information DB on the basis of the value, which is input by the user, corresponding to the audio device information. The controller 580 may directly download frequency information recorded in an audio device, which is connected through Bluetooth and the like, from the audio device to update the audio device information DB.

In step 1315, the controller 580 creates audio compensation information on the basis of the result of performing the updating mode and registers the created audio compensation information.

In step 1317, the controller 580 converts an audio output characteristic related to the current connected audio device on the basis of the created audio compensation information.

In step 1319, the controller 580 processes an audio output on the basis of the audio output characteristic converted in step 1309 or step 1317.

Figure 14:
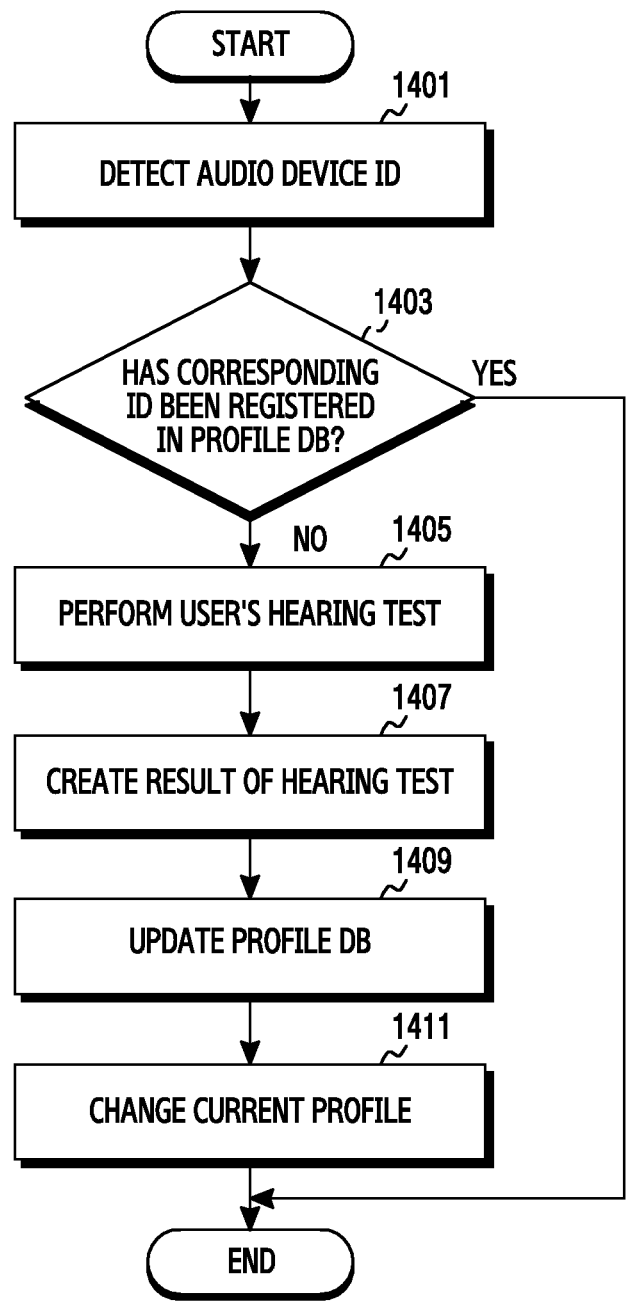
FIG. 14 is a flowchart illustrating a method for creating audio compensation information in an electronic device according to an embodiment of the present disclosure.

FIG. 14 is a flowchart illustrating a method for creating audio compensation information in an electronic device according to various embodiments of the present disclosure.

Referring to FIG. 14, FIG. 14 illustrates an example of performing an updating mode on the basis of a hearing test.

In step 1401, when an audio device is connected, the controller 580 detects an ID of the connected audio device. For example, a user may operate an active audio device, such as a Bluetooth headphone, to be connected to the electronic device 500 through Bluetooth communication. When detecting the audio device connection through the Bluetooth communication, the controller 580 may confirm a device identifier which is provided from the audio device at the time of establishing Bluetooth communication connection (e.g. a pairing process).

In step 1403, the controller 580 determines whether the ID of the connected audio device is registered in a pre-established profile DB. For example, the controller 580 may determine whether the ID of the audio device is registered in a profile DB of the electronic device 500, such as the above-described Table 1.

When it is determined, in step 1403, that the ID of the audio device is registered in the profile DB ("Yes" in step 1403), the controller 580 changes, in step 1411, a currently established profile by using a profile registered in the profile DB, as described above, without performing an update.

When it is not determined in step 1403 that the ID of the audio device is registered in the profile DB, the controller 580 performs, in step 1405, a hearing test for testing a user's hearing. For example, when an ID corresponding to the connected audio device is not found in the profile DB, the controller 580 performs the update. When performing the update, the controller 580 may provide a user interface, as shown in FIG. 17 described below, and may perform a hearing test through interaction with the user on the basis of the user interface. The user may be wearing an audio device connected to the electronic device 500 (e.g. wearing a Bluetooth headphone or headset).

In step 1407, the controller 580 determines the result of the user's hearing test related to the audio device. For example, the controller 580 may determine the user's hearing characteristics related to the currently connected audio device, and may create a profile corresponding to the determined hearing characteristics.

In step 1409, the controller 580 updates the profile DB on the basis of the result of the hearing test. The controller 580 may additionally register, in the profile DB, an ID of the connected audio device and a profile in which the user's hearing characteristics are considered with respect to the corresponding audio device. For example, the profile DB, such as shown in Table 1, may be updated by adding the ID of the audio device and the profile to the profile DB.

In step 1411, the controller 580 changes the currently established profile by using a profile registered in the profile DB.

Figure 15:
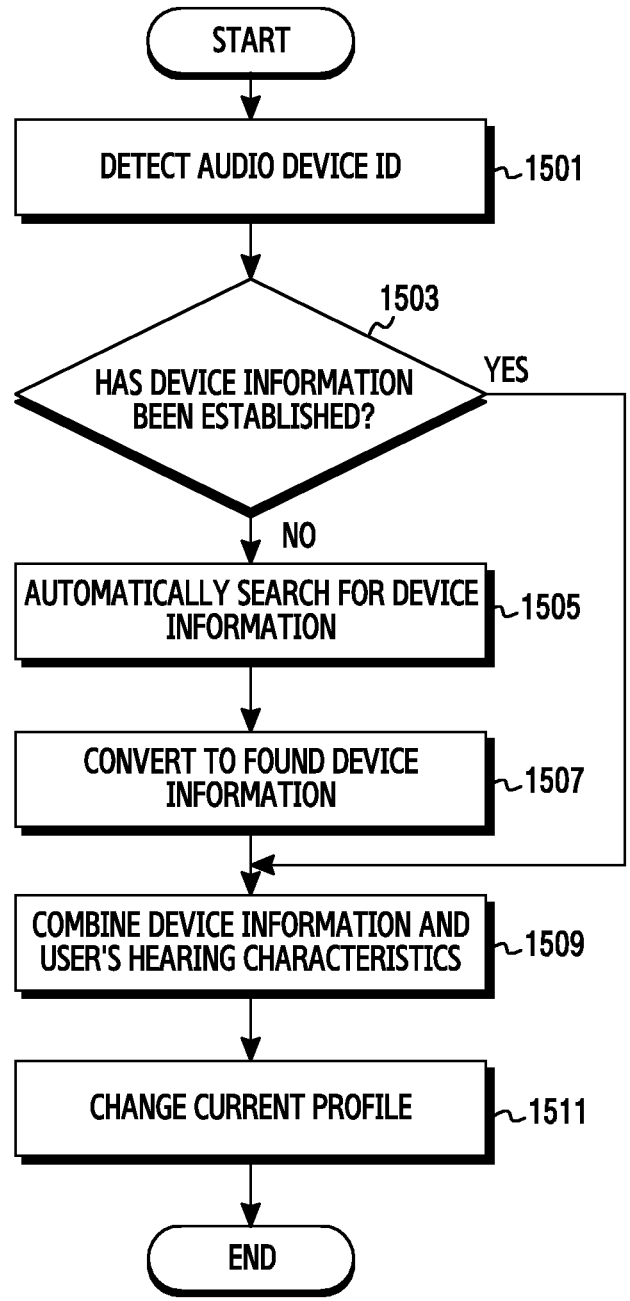
FIG. 15 is a flowchart illustrating a method for creating audio compensation information in an electronic device according to another embodiment of the present disclosure.

FIG. 15 is a flowchart illustrating a method for creating audio compensation information in an electronic device according to various embodiments of the present disclosure.

Referring to FIG. 15, FIG. 15 illustrates an example of automatically performing an update on the basis of device information (e.g. frequency information) of an audio device.

In step 1501, when an audio device is connected, the controller 580 detects an ID of the connected audio device. For example, a user may operate an active audio device, such as a Bluetooth headphone, connected to the electronic device 500 through Bluetooth communication. When it is detected that the audio device has been connected through Bluetooth communication, the controller 580 may confirm a device identifier and device information (e.g. frequency information), which are provided from the audio device at the time of establishing Bluetooth communication connection (e.g. a pairing process).

In step 1503, the controller 580 determines whether the device information (e.g. frequency information) of the connected audio device corresponds to the currently established device information. The controller 580 may determine whether the device information of the connected audio device matches the device information currently established in the electronic device 500.

When it is determined, in step 1503, that the device information of the audio device corresponds to the currently established device information ("Yes" in step 1503), the controller 580 changes, in steps 1509 and 1511, a current profile by using the currently established device information, as described above, without performing an update. The controller 580 may combine, in step 1509, frequency information of an audio device, which is connected to the electronic device, and a user's pre-established hearing characteristics by a method such as convolution to create a profile, and may change, in step 1511, a currently established profile by using the created profile. A profile, in which the frequency information of the audio device and the user's hearing characteristics are combined by a method such as convolution, may be registered in advance, or may be created in real time, as illustrated in FIG. 17.

According to various embodiments of the present disclosure, a convolution method for creating a profile may be implemented, and will be described below with reference to FIGS. 18, 19, and 20.

Figure 18A:
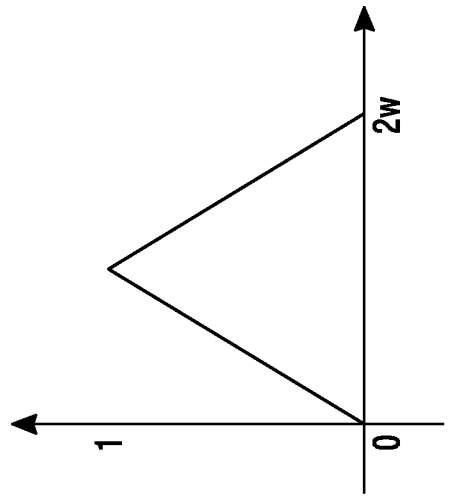
FIG. 18A illustrates a convolution method for creating a profile in an electronic device according to an embodiment of the present disclosure.

FIG. 18A illustrates a convolution method for creating a profile in an electronic device according to an embodiment of the present disclosure.

Figure 18B:
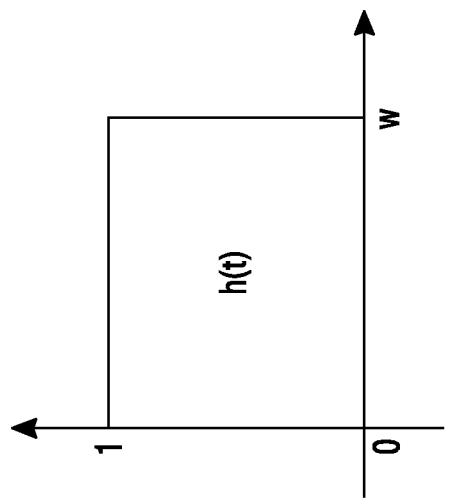
FIG. 18B illustrates a convolution method for creating a profile in an electronic device according to another embodiment of the present disclosure.

FIG. 18B illustrates a convolution method for creating a profile in an electronic device according to another embodiment of the present disclosure.

Figure 18C:
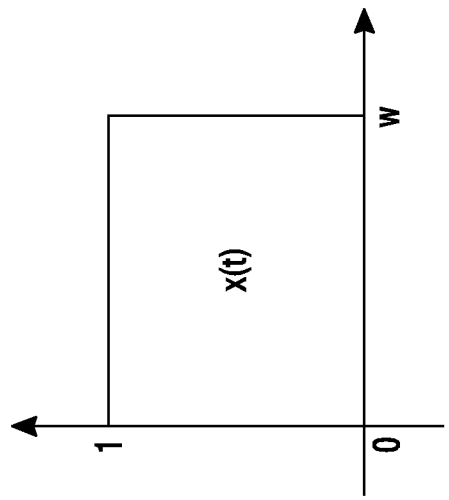
FIG. 18C illustrates a convolution method for creating a profile in an electronic device according to another embodiment of the present disclosure.

FIG. 18C illustrates a convolution method for creating a profile in an electronic device according to another embodiment of the present disclosure.

Referring to FIGS. 18A to 18C, the convolution is a method for analyzing a signal in a time domain. For example, in the case where one signal (frequency information) has a relative time change with reference to another signal (e.g. hearing characteristics), the convolution may indicate a signal (e.g. profile) calculated through integration. Examples of such a convolution are shown in Equation (1) and Equation (2) below.

$$y(t)=x(t)*h(t)=\int_{-\infty}^{+\infty}x(\tau)h(t-\tau)d\tau \qquad \text{Equation (1)}$$

$$x(t)*h(t)=X(w) \times H(w) \qquad \text{Equation (2)}$$

In Equation (1), when h(t) is a signal which represents an operation of a system, y(t) may represent a state in which a signal passed through the system is changed. y(t) may refer to a process of synthesizing (combining) two different signals. For example, a convolutional integration of a time domain is converted via Fourier transform (FT) or fast Fourier transform (FFT) into a frequency domain as shown in Equation (1) and a value may be calculated through a multiplication calculation as shown in Equation (2). In Equations (1) and (2), the symbol "*" may indicate a convolution calculation and the symbol "×" may indicate a multiplication calculation.

According to an embodiment of the present disclosure, in a convolution method, various signals are convoluted to analyze a signal in the time domain. For example, referring to FIGS. 18A to 18C, when two signals (e.g. x(t), h(t)) are completely overlapped as in the graph of FIG. 18A and the graph of FIG. 18B, a signal as in the graph of FIG. 18C may be output. For example, a cycle is changed to be twice as long (2w) and a triangular wave signal, a peak (or maximum value, peak value, which is a value of a signal when the signal is maximized) of which is "1", may be created.

Figure 19:
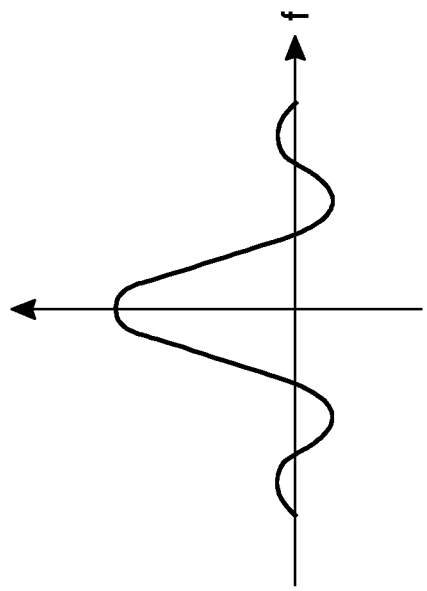
FIG. 19 illustrates a convolution method for creating a profile in an electronic device according to another embodiment of the present disclosure.
Figure 19:
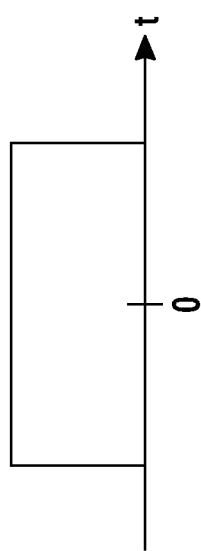

FIG. 19 illustrates a convolution method for creating a profile in an electronic device according to another embodiment of the present disclosure.

FIG. 20 illustrates a convolution method for creating a profile in an electronic device according to another embodiment of the present disclosure.

According to an embodiment of the present disclosure, as illustrated in FIG. 19, a square wave may be used as an input signal. When a Fourier transform is performed on the square wave on a time axis, the square wave may be represented as a Sinc (sinus cardinalis (cardinal sine)) signal (function) on the frequency axis. For example, a shape may be shown on the frequency axis according to a Fourier transform on a triangular wave. In other words, multiplication on the time axis may indicate a convolution on the frequency axis, and multiplication on the frequency axis may indicate a convolution on the time axis. In other words, multiplication and convolution may have a relation of duality (e.g. principle of duality) between them. Referring to FIG. 20, a convolution of two square waves on the time axis is shown as a triangular wave on the time axis. This may indicate that an area overlapping when one figure is symmetrical about the "y" axis is expressed as a value. Further, the convolution may be shown as $Sinc^2$ (square of Sinc) on the frequency axis.

Referring to FIG. 19 again, when the device information (e.g. frequency information) of the audio device does not correspond to the currently established device information in step 1503 ("No" in step 1503), the controller 580 may automatically search for device information in step 1505. For example, the controller 580 may search for device information of a connected audio device in the audio device information DB, such as in Table 2. According to various embodiments of the present disclosure, when the device information of the connected audio device is not stored in the audio device information DB, the device information of the connected audio device may be replaced with the currently established device information or device information established as a default. Further, when the device information of the connected audio device is not stored in the audio device information DB, the controller 580 may be connected to another external electronic device (e.g. an external server for managing device information according to each audio device) to acquire the device information. The controller 580 may map an ID of the connected audio device and the acquired device information to update the audio device information DB. For example, the controller 580 may additionally store the ID of the audio device and the acquired frequency information in the audio device information DB, such as in Table 2.

In step 1507, the controller 580 may change the currently established device information by using the stored device information. For example, the controller 580 may establish the stored device information as current device information of the electronic device 500.

In step 1509, the controller 580 may combine the device information and the user's pre-established hearing characteristics by such a method as convolution. According to an embodiment of the present disclosure, the controller 580 may combine frequency information and the user's hearing characteristics by such a method as convolution to create a profile.

In step 1511, the controller 580 may change a current profile on the basis of a profile in which device information and hearing characteristics are considered and compensated for.

Figure 16:
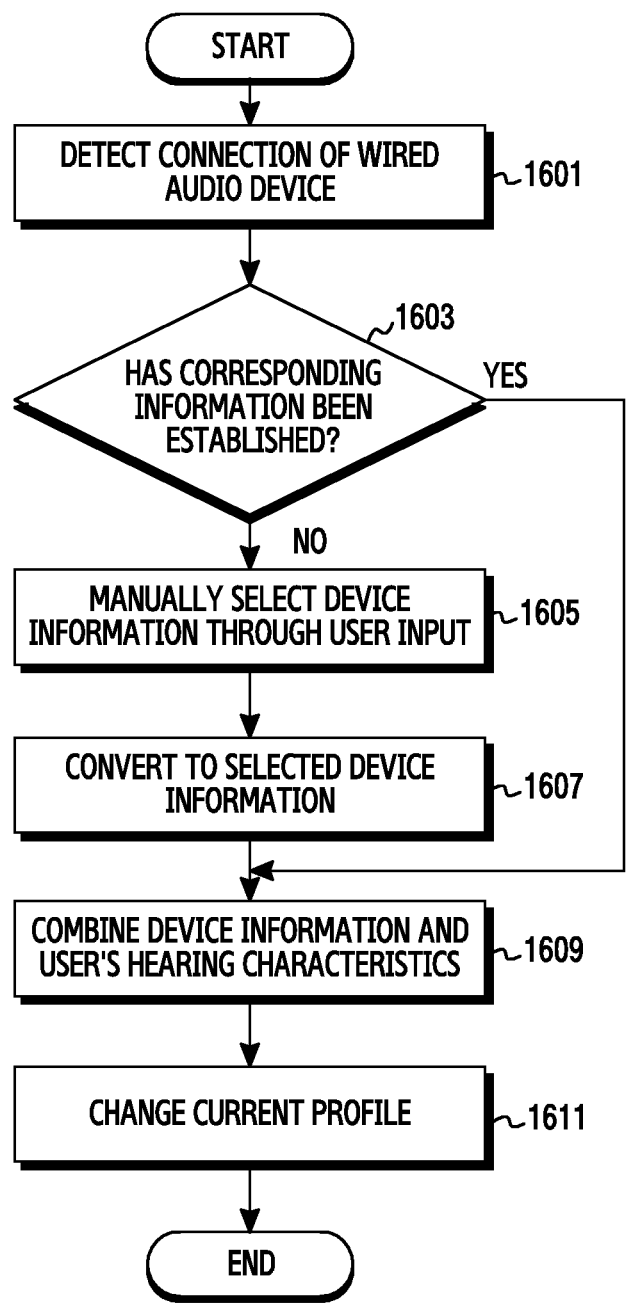
FIG. 16 is a flowchart illustrating a method for creating audio compensation information in an electronic device according to another embodiment of the present disclosure.

FIG. 16 is a flowchart illustrating creating audio compensation information in an electronic device according to various embodiments of the present disclosure.

Referring to FIG. 16, FIG. 16 illustrates an example of manually performing an updating mode on the basis of device information (e.g. frequency information) of an audio device in various embodiments.

In step 1601, the controller 580 detects the connection of a wired audio device. For example, the user may connect a passive audio device, such as a wired earphone, through an interface (e.g. connector) of the electronic device 500. When detecting the connection of the audio device through the interface, the controller 580 may detect the corresponding resistance information (e.g. resistance values, such as 16 ohm, 32 ohm, 300 ohm) in response to resistance configured in the audio device. According to various embodiments of the present disclosure, when detecting the connection of the wired audio device, the controller 580 may determine the resistance of each audio device by using impedance detection, and may determine device information (e.g. frequency information) related to the corresponding audio device on the basis of the determined resistance. Device information of each passive audio device may be determined on the basis of a mapping table in which device information is mapped according to various resistances of the passive audio device.

In step 1603, the controller 580 determines whether the device information (e.g. frequency information) of the connected audio device corresponds to the currently established device information. According to an embodiment of the present disclosure, the controller 580 may determine whether the device information of the currently connected audio device matches the device information currently established in the electronic device 500.

When it is determined, in step 1603, that the device information of the audio device corresponds to the currently established device information ("Yes" in step 1603), the controller 580 changes, in steps 1609 and 1611, a profile by using the currently established device information, as described above, without performing an update. According to an embodiment of the present disclosure, the controller 580 combines, in step 1609, frequency information of an audio device, which is connected to the electronic device, and a user's pre-established hearing characteristics by a method such as convolution to create a profile, and changes, in step 1611, a currently established profile by using the created profile. A profile, in which the frequency information of the audio device and the user's hearing characteristics are combined by a method such as convolution, may be registered in advance, or may be created in real time, as illustrated in FIG. 16. The convolution method as described with respect to FIGS. 18A, 18B, 18C, 19, and 20 in the above-described FIG. 15 may be used.

When the device information (e.g. frequency information) of the audio device does not correspond to the currently established device information in step 1603 ("No" in step 1603), the controller 580 manually selects device information in step 1605. For example, the controller 580 may display, through a user interface, a list of device information corresponding to an audio device information DB, such as in Table 3, and may receive selection of particular device information from a user through the user interface. According to an embodiment of the present disclosure, the user may select device information corresponding to a wired earphone connected to the electronic device 500 in the user interface of the electronic device 500, while wearing the wired earphone. The user may select, on the basis of a device name (e.g. product name), the device information corresponding to the connected audio device in the user interface.

In step 1607, the controller 580 changes the currently established device information by using the selected device information. For example, the controller 580 may establish the selected device information as current device information of the electronic device 500.

In step 1609, the controller 580 combines the changed established device information and the user's pre-established hearing characteristics by a method such as convolution. According to an embodiment of the present disclosure, the controller 580 may combine frequency information and the user's hearing characteristics by a method such as convolution to create a profile.

In step 1611, the controller 580 changes a current profile on the basis of a profile in which device information and hearing characteristics are considered and compensated for.

Figures 17A, 17B:
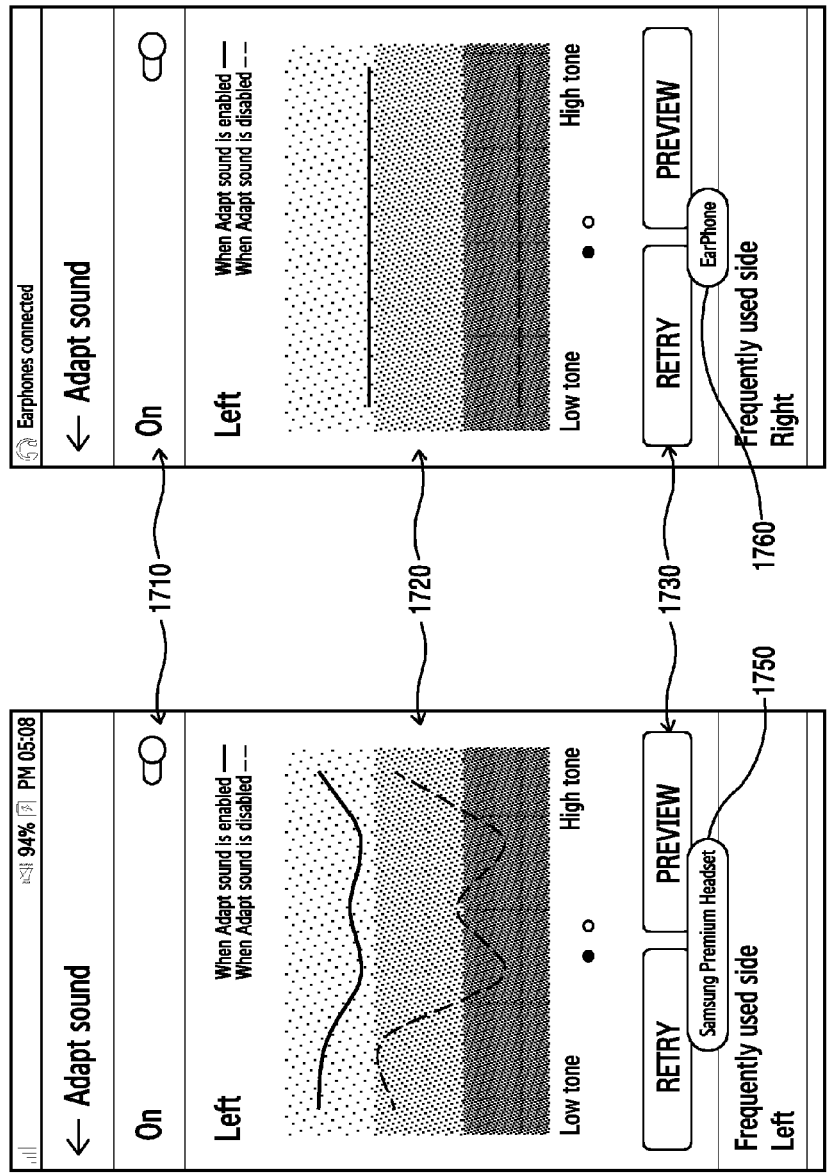
FIG. 17A illustrates a user interface for establishing an audio output in an electronic device according to an embodiment of the present disclosure.
FIG. 17B illustrates a user interface for establishing an audio output in an electronic device according to another embodiment of the present disclosure.

FIG. 17A illustrates a user interface for establishing an audio output in an electronic device according to an embodiment of the present disclosure;

FIG. 17B illustrates a user interface for establishing an audio output in an electronic device according to another embodiment of the present disclosure;

Referring to FIGS. 17A and 17B, FIGS. 17A and 17B illustrate, in various embodiments, an example of a user interface for a hearing test for applying a user's hearing characteristics to an audio device connected to the electronic device 500. Examples of FIGS. 17A and 17B may be to show screenshots in which the hearing test is completed, a profile related to the corresponding audio device is registered in a profile DB, and the result of the registration is provided in response to a user selection or the detection of the audio device connection.

As illustrated in FIGS. 17A and 17B, the user interface includes a configuration area 1710 that may configure sound quality optimized to a user's ears and configure (e.g. turn on/turn off) whether to use a function of outputting audio (e.g. adapt sound function), a first information area 1720 that provides an optimized sound quality state to an audio device through a hearing test, a function selection area 1730 including a button (e.g. RETRY button) for reconfiguring sound quality optimized to the audio device (e.g. performing the hearing test again) and a button (e.g. PREVIEW button) for previewing audio which is output on the basis of currently configured optimized sound quality (e.g. profile), a second information area 1740 that provides configured information in a direction (side) which is frequently used by the user, and a notification window 1750 or 1760 that provides information on an audio device currently connected to the electronic device 500.

According to various embodiments of the present disclosure, the notification window 1750 or 1760 may be provided when the audio device is connected, and may provide information corresponding to the connected audio device. For example, FIG. 17A illustrates a case in which an active audio device (e.g. Bluetooth headphone) is connected and information thereon (e.g. Samsung Premium Headset) is provided through the notification window 1750. FIG. 17B illustrates a case in which a passive audio device (e.g. wired earphone) is connected and information thereon (e.g. earphone) is provided through the notification window 1760. The notification windows 1750 and 1760 may provide information on a currently connected audio device in the form of a pop-up window.

According to various embodiments of the present disclosure, an operation method of an electronic device includes detecting a connection to an audio device, acquiring identification information and/or characteristics of the audio device, at least partially based on the connection to the audio device, selecting pre-stored audio adaptation information, at least partially based on the acquired information and/or characteristics, changing an audio signal, at least partially based on the audio adaptation information, and transmitting the changed audio signal to the audio device.

According to various embodiments of the present disclosure, the operation method further includes wirelessly receiving the identification information of the audio device from the audio device. The operation method further includes acquiring an impedance characteristic of the audio device and/or audio device information and determining the characteristics of the audio device, when the audio device is connected through the wired interface. The operation method further includes providing a selected audio to the audio device after a connection to the audio device, receiving a user response to the audio through the user interface, and creating the audio adaptation information, at least partially based on the received response.

An operation method of an electronic device, according to various embodiments of the present disclosure, include detecting a connection to an audio device, determining audio adaptation information related to the audio device in response to the connection of the audio device, correcting an audio output corresponding to the audio device on the basis of the audio adaptation information when the audio adaption information has been registered, updating the audio adaptation information related to the audio device when the audio adaption information has not been registered, and correcting an audio output corresponding to a characteristic of the audio device on the basis of the updated audio adaptation information.

According to various embodiments of the present disclosure, the audio adaptation information includes a profile for compensating for an audio output characteristic according to each audio device, or frequency information of the audio device.

According to various embodiments of the present disclosure, the updating of the audio adaptation information of the electronic device includes combining a unique frequency characteristic of the audio device and a user's hearing characteristics by a method such as convolution to update the audio adaptation information.

According to various embodiments of the present disclosure, the updating of the audio adaptation information of the electronic device includes providing a user interface when determining to perform the hearing test, performing a hearing test which combines the frequency characteristic of a connected audio device and a user's hearing characteristics by a method such as convolution according to an interaction with the user based on the user interface, and creating a profile related to the connected audio device on the basis of the result of the hearing test. The operation method of the electronic device further includes converting a current profile currently established in the electronic device to the created profile, and converting and outputting audio characteristics on the basis of the converted profile.

According to various embodiments of the present disclosure, the determining of the audio adaptation information of the electronic device includes determining whether to perform, in response to the detection of the audio device connection, a hearing test or perform audio output characteristic conversion based on pre-established audio adaptation information.

According to various embodiments of the present disclosure, the updating of the audio adaptation information of the electronic device includes determining the frequency information of a connected audio device in response to the audio device connection, combining currently established frequency information and a user's hearing characteristics by a method such as convolution when the frequency information of the audio device corresponds to the currently established frequency information, automatically searching for the frequency information of the connected audio device in an audio device information DB when the frequency information of the audio device does not correspond to the currently established frequency information, converting the currently established frequency information to the stored frequency information, and combining the converted frequency information, and the user's hearing characteristics by a method such as convolution.

According to various embodiments of the present disclosure, the updating of the audio adaptation information of the electronic device includes providing a list of audio devices with reference to the audio device information DB when the frequency information of the audio device does not correspond to the currently established frequency information, converting the currently established frequency information to frequency information manually selected by the user on the basis of the list, and combining the converted frequency information and the user's hearing characteristics by a method such as convolution. The operation method of the electronic device includes creating a profile by a combination through a method such as convolution and converting a current profile established in the electronic device to the created profile, and converting and outputting audio characteristics on the basis of the converted profile.

According to various embodiments of the present disclosure, the electronic device includes a wired or wireless interface configured to establish a connection to an audio device, a memory, and one or more processors electrically connected to the memory and the wired or wireless interface. The memory includes a profile DB which stores device information of the audio device and a profiles and an audio device information DB which stores the device information and frequency information of the audio device.

According to various embodiments of the present disclosure, an operation method of an electronic device may be configured such that the one or more processors performs establishing audio adaptation information on the basis of a frequency characteristic of an audio device and a user's hearing characteristics, detecting a connection to the audio device, determining audio adaptation information related to a connected audio device, converting a currently established audio output characteristic to an audio output characteristic corresponding to the connected audio device on the basis of the determined audio adaptation information, and processing an audio output on the basis of the converted audio output characteristic.

In order to solve the above-described technical problem, a method and apparatus for outputting audio in an electronic device according to various embodiments of the present disclosure may reflect a user's hearing characteristics according to each audio device to automatically compensate for the user's hearing characteristics and provide an output audio. A user may listen to audio optimized on the basis of the characteristics of an audio device and the user's hearing characteristics. Therefore, the user may listen to audio which has better sound quality and volume.

The embodiments of the present disclosure disclosed herein and shown in the drawings are examples presented in order to describe technical details of the present disclosure and to help the understanding of the present disclosure, but do not limit the scope of the present disclosure. Therefore, it should be construed that, in addition to the embodiments disclosed herein, all modifications and changes or modified and changed forms derived from the technical idea of the present disclosure fall within the scope of the present disclosure as defined by the appended claims and their equivalents.

What is claimed is:

1. An electronic device comprising:
an audio interface configured to establish a connection to an audio device;
a memory configured to store instructions; and
at least one processor, operatively coupled to the memory and the audio interface,
wherein the at least one processor is configured to execute the stored instructions to:
identify the audio device, based on an established connection;
identify audio adaptation information determined based on a frequency characteristic of the audio device and a hearing characteristic of a user of the electronic device;
determine, based on identifying the audio device, whether the audio device corresponds to a pre-registered audio device or not;
upon determining that the audio device corresponds to the pre-registered audio device, identify the audio adaptation information from the data that has been registered in the electronic device;
upon determining that the audio device does not correspond to the pre-registered audio device, determine the audio adaptation information by combining the frequency characteristic of the audio device and the hearing characteristic of the user; and
output, via the audio device, an audio signal, at least partially based on the identified audio adaptation information.

2. The electronic device of claim 1, wherein the at least one processor is configured to execute the stored instructions to:
wirelessly receive, based on the established connection, identification information of the audio device from the audio device; and
identify the audio device based on the received identification information.

3. The electronic device of claim 1, wherein the at least one processor is configured to execute the stored instructions to:
if the connection is by wire, identify the audio device by acquiring at least one of an impedance characteristic of the audio device or information on the audio device to determine characteristics of the audio device.

4. The electronic device of claim 1, further comprising:
a display,
wherein the at least one processor is further configured to execute the stored instructions to:
provide selected audio to the audio device;
receive a response to the selected audio through a user interface presented via the display, the response corresponding to at least one of the frequency characteristic or the hearing characteristic of the user; and
generate the audio adaptation information, at least partially based on the received response.

5. The electronic device of claim 1, wherein the at least one processor is further configured to execute the stored instructions to determine whether to perform a hearing test for establishing the audio adaptation information or perform an audio output characteristic conversion based on stored audio adaptation information.

6. The electronic device of claim 5, further comprising:
a display,
wherein the at least one processor is further configured to execute the stored instructions to:
provide, via the display, a user interface when the processor determines to perform the hearing test;
perform the hearing test by combining the frequency characteristic of the audio device with the hearing characteristic of the user according to a user's interaction on the user interface;

generate a profile related to the audio device based on the result of the hearing test; and convert a profile, currently established in the electronic device, to the generated profile.

7. The electronic device of claim 1,
wherein the memory stores:
a profile database (DB) configured to store a profile of the audio device associated with device information of the audio device; and
an audio device information DB configured to store frequency information of the audio device associated with the device information of the audio device, and
wherein the at least one processor is further configured to execute the stored instructions to:
determine frequency information of the audio device based on the frequency characteristic of the audio device;
combine currently established frequency information and the hearing characteristic of the user when the determined frequency information corresponds to the currently established frequency information; and
search for the frequency information stored in the audio device information DB when the determined frequency information does not correspond to the currently established frequency information, convert the currently established frequency information to the determined frequency information, and generate a profile by combining the converted frequency information and the hearing characteristic of the user.

8. The electronic device of claim 7, wherein the at least one processor is further configured to:
provide a list of audio devices associated with the audio device information DB when the determined frequency information does not correspond to the currently established frequency information; and
convert the currently established frequency information to frequency information selected by the user based on the list of audio devices.

9. A method of an electronic device, the method comprising:
establishing a connection to an audio device;
identifying the audio device based on the established connection;
identifying audio adaptation information determined based on a frequency characteristic of the audio device and a hearing characteristic of a user of the electronic device;
determining, based on identifying the audio device, whether the audio device corresponds to a pre-registered audio device or not;
upon determining that the audio device corresponds to the pre-registered audio device, identifying the audio adaptation information from data that has been registered in the electronic device;
upon determining that the audio device does not correspond to the pre-registered audio device, determining the audio adaptation information by combining the frequency characteristic of the audio device and the hearing characteristic of the user; and
outputting, via the audio device, an audio signal, at least partially based on the audio adaptation information.

10. The method of claim 9, wherein the identifying the audio device comprises:
if the connection is by wire, identifying the audio device by acquiring at least one of an impedance characteristic of the audio device or information on the audio device to determine the characteristics of the audio device.

11. The method of claim 9, further comprising:
providing selected audio to the audio device;
receiving a response to the selected audio through a user interface presented via a display of the electronic device, the response corresponding to at least one of the frequency characteristic or the hearing characteristic of the user; and
generating the audio adaptation information, at least partially based on the received response.

12. The method of claim 9, further comprising:
determining whether to perform a hearing test for establishing the audio adaptation information or perform an audio output characteristic conversion based on stored audio adaptation information.

13. The method of claim 12, further comprising:
providing, via a display of the electronic device, a user interface when it is determined to perform the hearing test;
performing the hearing test by combining the frequency characteristic of the audio device with the hearing characteristic of the user according to a user's interaction on the user interface;
generating a profile related to the audio device based on the result of the hearing test; and
converting a profile currently established in the electronic device, to the generated profile.

14. The method of claim 9, wherein the electronic device stores:
a profile database (DB) configured to store a profile of the audio device associated with device information of the audio device; and
an audio device information DB configured to store frequency information of the audio device associated with the device information of the audio device, and
wherein the method further comprises:
determining frequency information of the audio device based on the frequency characteristic of the audio device;
combining currently established frequency information and the hearing characteristic of the user when the determined frequency information corresponds to the currently established frequency information; and
searching for the frequency information stored in the audio device information DB when the determined frequency information does not correspond to the currently established frequency information, converting the currently established frequency information to the determined frequency information, and generating a profile by combining the converted frequency information and the hearing characteristic of the user.

15. The method of claim 14, further comprising:
providing a list of audio devices associated with the audio device information DB when the determined frequency information does not correspond to the currently established frequency information; and
converting the currently established frequency information to frequency information selected by the user based on the list of audio devices.

* * * * *